US012495991B2

(12) United States Patent
Bhimavarapu et al.

(10) Patent No.: US 12,495,991 B2
(45) Date of Patent: Dec. 16, 2025

(54) PATIENT VIDEO MONITORING SYSTEM

(71) Applicant: Stryker Corporation, Kalamazoo, MI (US)

(72) Inventors: Krishna Sandeep Bhimavarapu, Kalamazoo, MI (US); Jeremy L. Dunn, Portage, MI (US); Lavanya Vytla, McKinney, TX (US); Nikhil Mishra, Portage, MI (US); Faisal Mahmood, Portage, MI (US); Ross Michael Nave, Kalamazoo, MI (US); Jerald A. Trepanier, Augusta, MI (US)

(73) Assignee: Stryker Corporation, Portage, MI (US)

( * ) Notice: Subject to any disclaimer, the term of this patent is extended or adjusted under 35 U.S.C. 154(b) by 179 days.

(21) Appl. No.: 18/572,669

(22) PCT Filed: Jun. 28, 2022

(86) PCT No.: PCT/US2022/035359
§ 371 (c)(1),
(2) Date: Dec. 20, 2023

(87) PCT Pub. No.: WO2023/278478
PCT Pub. Date: Jan. 5, 2023

(65) Prior Publication Data

US 2024/0366114 A1 Nov. 7, 2024

Related U.S. Application Data

(60) Provisional application No. 63/218,053, filed on Jul. 2, 2021, provisional application No. 63/216,298, filed on Jun. 29, 2021.

(51) Int. Cl.

| | |
|---|---|
| ***A61B 5/11*** | (2006.01) |
| ***A61B 5/00*** | (2006.01) |
| ***G08B 21/04*** | (2006.01) |

(52) U.S. Cl.
CPC .......... *A61B 5/1128* (2013.01); *A61B 5/6891* (2013.01); *G08B 21/0476* (2013.01)

(58) Field of Classification Search
CPC ... A61B 5/0077; A61B 5/1117; A61B 5/1128; A61B 5/6891; A61G 7/10;
(Continued)

(56) References Cited

U.S. PATENT DOCUMENTS 6,128,522 A * 10/2000 Acker .................... A61B 5/055 335/298
6,679,830 B2 1/2004 Kolarovic et al.
(Continued)

FOREIGN PATENT DOCUMENTS

WO 2017/196695 A2 11/2017
WO 2020/264140 A1 12/2020

OTHER PUBLICATIONS

Intel RealSense Product Family D400 Series Datasheet, Jun. 2020, 127 pages, Revision 009, Intel.
(Continued)

*Primary Examiner* — Peter D Le
(74) *Attorney, Agent, or Firm* — Gardner, Linn, Burkhart & Ondersma LLP

(57) ABSTRACT

A monitoring system for a patient and/or patient support apparatus includes one or more cameras that capture images and depth data. A computer processes the image signals and depth data and performs one or more of the following functions: (a) enabling/disabling a remote control adapted to move a component of the patient support apparatus; (b) detecting patient breathing abnormalities; (c) detecting the presence of a ligature and its attendant strangulation risk to the patient; (d) identifying a sheet and/or a patient gown in the captured images; (e) disabling/enabling controls on the patient support apparatus based on patient position; (f)
(Continued)

synchronizing readings from one or more sensors with the image signals; (g) stitching together images captured from multiple cameras; and/or other functions. The cameras may be positioned on the patient support apparatus and/or elsewhere, and the computer may be a server and/or a controller on the patient support apparatus.

20 Claims, 12 Drawing Sheets

(58) Field of Classification Search
CPC ............ G08B 21/0461; G08B 21/0476; G16H 30/20; G16H 30/40; G16H 40/67
See application file for complete search history.

(56) References Cited

U.S. PATENT DOCUMENTS 7,319,386 B2 1/2008 Collins, Jr. et al.
8,437,876 B2 5/2013 Receveur et al.
9,204,823 B2 12/2015 Derenne et al.
9,381,125 B2 7/2016 Herbst et al.
9,530,080 B2 12/2016 Glazer
9,536,310 B1 1/2017 Kusens
9,635,320 B2 4/2017 Greco et al.
9,741,227 B1 8/2017 Kusens
9,794,523 B2 10/2017 Greco et al.
9,866,797 B2 1/2018 Clark et al.
9,905,113 B2 2/2018 Kusens
10,037,669 B2 7/2018 Hanson
10,044,989 B2 8/2018 Greco et al.
10,078,951 B2 9/2018 Kusens
10,096,223 B1 10/2018 Kusens
10,121,070 B2 11/2018 Derenne et al.
10,165,230 B2 12/2018 Glazer
10,210,395 B2 2/2019 Kusens
10,217,342 B2 2/2019 Kusens
10,229,571 B2 3/2019 Kusens
10,238,292 B2 * 3/2019 Vanderpohl, III ... A61B 5/6891
10,368,039 B2 7/2019 Derenne et al.
10,382,727 B2 8/2019 Clark et al.
10,410,500 B2 9/2019 Derenne et al.
10,546,481 B2 1/2020 Kusens
10,630,941 B2 4/2020 Greco et al.
10,645,349 B2 5/2020 Glazer
10,674,941 B2 6/2020 Tanaka et al.
10,679,748 B2 6/2020 Durlach et al.
10,708,550 B2 7/2020 Glazer et al.
10,750,129 B2 8/2020 Greiner et al.
10,786,183 B2 9/2020 Matsunaga et al.
10,825,315 B2 11/2020 Hanson et al.
10,904,492 B2 1/2021 Derenne et al.
10,905,609 B2 2/2021 Childs et al.
10,905,611 B2 2/2021 Sidhu et al.
10,932,970 B2 3/2021 Lightcap et al.
11,011,272 B2 5/2021 Durlach et al.
11,013,655 B1 * 5/2021 Ebrahimi Afrouzi .... A61G 7/08
11,032,521 B2 6/2021 Clark et al.
11,032,522 B2 6/2021 Clark et al.
2003/0052787 A1 * 3/2003 Zerhusen ................ G16Z 99/00 340/286.07
2005/0035862 A1 2/2005 Wildman et al.
2006/0181776 A1 * 8/2006 Sandhu ................ G02B 27/024 359/618
2007/0010719 A1 1/2007 Huster et al.
2009/0119843 A1 5/2009 Rodgers et al.
2010/0328443 A1 12/2010 Lynam et al.
2013/0283529 A1 10/2013 Hayes et al.
2014/0090172 A1 * 4/2014 Hyde ................... G05D 1/0227 5/600
2014/0094997 A1 4/2014 Hyde et al.
2014/0297327 A1 10/2014 Heil et al.
2015/0109442 A1 4/2015 Van Heerden et al.
2015/0281659 A1 * 10/2015 Hood ..................... H04N 7/188 348/143
2016/0088282 A1 3/2016 Sadi et al.
2016/0140827 A1 5/2016 Derenne et al.
2016/0338891 A1 11/2016 Agdeppa et al.
2016/0367415 A1 * 12/2016 Hayes .................. A61G 1/0275
2016/0367420 A1 12/2016 Zerhusen et al.
2018/0140230 A1 5/2018 Horita
2018/0218587 A1 8/2018 Wong et al.
2018/0286206 A1 10/2018 Kuramoto
2019/0046080 A1 2/2019 Nishikado et al.
2019/0147595 A1 5/2019 Hsu et al.
2019/0374417 A1 * 12/2019 Hiratsuka .............. A61G 13/06
2020/0211154 A1 7/2020 Ng et al.
2020/0228755 A1 7/2020 Greco et al.
2021/0049887 A1 2/2021 Hanson et al.
2021/0058587 A1 2/2021 Glazer et al.

OTHER PUBLICATIONS

Lin et al., "Wireless Battery-free Body Sensor Networks Using Near-field-enabled Clothing", Nature Communications, Jan. 23, 2020, 10 pages, Springer Nature.
International Search Report and Written Opinion, completed Sep. 7, 2022, for PCT/US22/35359.

* cited by examiner

PATIENT VIDEO MONITORING SYSTEM

CROSS-REFERENCE TO RELATED APPLICATIONS

This application claims priority to U.S. provisional patent application Ser. No. 63/216,298 filed Jun. 29, 2021, by inventors Krishna Bhimavarapu et al. and entitled PATIENT VIDEO MONITORING SYSTEM, and to U.S. provisional patent application Ser. No. 63/218,053 filed Jul. 2, 2012, by inventors Krishna Bhimavarapu et al. and entitled PATIENT VIDEO MONITORING SYSTEM, the complete disclosures of both of which are incorporated herein by reference.

BACKGROUND

The present disclosure relates to systems and methods utilizing video cameras for monitoring patients and their environment.

SUMMARY

According to various aspects of the present disclosure, a patient support apparatus, a system, and/or one or more methods are provided that operate in conjunction with one or more cameras adapted to monitor the patient and/or the patient's environment. The images from the camera are used to improve the safety of the patient, to help prevent one or more adverse events from occurring (e.g. patient fall), to prevent unauthorized usage of the patient support apparatus assigned to the patient, to detect patient conditions that warrant medical attention, to synchronize sensor readings with video captured from the cameras, to apprise remotely positioned caregivers of the patient's situations when an exit alert is detected, and to allow remote controlled-movement of the patient support apparatus to be carried out without risk of injury or damage to the patient support apparatus and/or the patient or other individuals. Still other features and aspects of the present disclosure will be apparent to one of ordinary skill in the art from the following written description and accompanying drawings.

According to one aspect of the present disclosure, a patient support apparatus is provided that includes a support surface, a movable component, a powered actuator adapted to move the movable component, a control panel, a transceiver, and a controller. The support surface is adapted to support a patient thereon. The control panel includes a movement control adapted to control the powered actuator. The transceiver is adapted to receive a movement command from a remote control positioned off-board the patient support apparatus. The controller communicates with the transceiver and a camera having a field of view that includes a range of motion of the component. The controller is adapted to drive the actuator in response to receiving the movement command if the camera is simultaneously capturing a video stream that includes the component, to not drive the actuator in response to the movement command if the camera is not simultaneously capturing the video stream, and to drive the actuator in response to the activation of the movement control on the control panel regardless of whether the camera is simultaneously capturing the video stream.

According to other aspects of the present disclosure, the camera may be positioned on the patient support apparatus.

In some embodiments, the transceiver is adapted to transmit the video stream to the remote control. The transceiver may further be adapted to receive an acknowledgement from the remote control of the receipt of the video stream. In such embodiments, the controller may be further adapted to drive the actuator in response to receiving the movement command if the camera is simultaneously capturing the video stream and the controller has received the acknowledgement from the remote control, and to not drive the actuator in response to receiving the movement command if the camera is simultaneously capturing the video stream but the controller has not received the acknowledgement from the remote control.

The movable component, in some embodiments, is a litter frame supported by a pair of lifts. The litter frame supports the support surface.

In some embodiments, the support surface includes a Fowler section adapted to pivot about a generally horizontal axis, and the movable component is the Fowler section.

The transceiver, in some embodiments, is a WiFi transceiver adapted to communicate with a wireless access point of a local area network of a healthcare facility.

The remote control, in some embodiments, is an electronic device that is adapted to communicate with the wireless access point of the local area network, and that is further adapted to send the movement command to a server on the local area network that then forwards the movement command to the patient support apparatus.

In some embodiments, the camera includes a depth sensor adapted to determine distances to objects appearing within the field of view of the camera.

In some embodiments, a second camera is positioned onboard the patient support apparatus. The controller, in such embodiments, may be adapted to generate a stitched video stream comprised of a portion of the video stream from the first camera and a portion of a second video stream from the second camera.

The patient support apparatus, in some embodiments, further comprises a second control panel that includes a second control adapted to carry out a particular function when activated. The second control is positioned on a face of the second control panel that faces away from the patient when the patient is positioned on the support surface. In such embodiments, the controller may be further adapted to analyze the video stream to determine if the patient is attempting to activate the second control panel and to disable the second control if the controller determines that the patient is attempting to activate the second control.

In some embodiments, the patient support apparatus further comprises an exit detection system and the second control is adapted to disarm the exit detection system when the second control is activated.

In some embodiments, the patient support apparatus further comprises an onboard monitoring system adapted to monitor a plurality of conditions on the patient support apparatus and to issue an alert if at least one of the conditions is in an undesired state, and to not issue the alert if none of the conditions are in the undesired state. In such embodiments, the second control may be adapted to disarm the onboard monitoring system when the second control is activated.

The controller, in some embodiments, is further adapted to analyze the video stream to determine a breathing rate of the patient. In such embodiments, the controller may be further adapted to perform any one or more of the following: transmit the breathing rate to a server on a local area network of a healthcare facility; transmit an alert to the server if the breathing rate exceeds an upper threshold; or transmit an alert to the server if the breathing rate decreases below a lower threshold.

In some embodiments, the controller is further adapted to analyze the video stream to determine if a ligature is present within the field of view. In such embodiments, the controller may be further adapted to transmit a message to a server on a local area network of a healthcare facility if the controller detects the presence of the ligature.

The controller, in some embodiments, is further adapted to communicate with a database containing visual characteristics of gowns assigned to patients within a healthcare facility in which the patient support apparatus is positioned, and to use the visual characteristics to identify within the video stream a gown worn by the patient.

The controller, in some embodiments, is further adapted to analyze the video stream to determine a position of the patient's body, to modify a color of the patient's body within the video stream, and to transmit the modified video stream with the modified color of the patient's body to an off-board device.

The modified color, in some embodiments, is comprised of shades of a single color, such as, but not limited to, gray.

In some embodiments, the off-board device is a server on a local area network of a healthcare facility in which the patient support apparatus is positioned.

The controller, in some embodiments, is further adapted to identify the patient support apparatus in the video stream, to modify the video stream by replacing the patient support apparatus with a computer generated rendering of the patient support apparatus, and to transmit the modified video stream to an off-board device.

The patient support apparatus, in some embodiments, further comprises an exit detection system comprising a plurality of load cells, and the controller is further adapted to generate a synchronized data file including a visual representation of readings from the plurality of load cells synchronized with movement of the patient captured in the video stream. In such embodiments, the controller may be further adapted to transmit the synchronized data file to an off-board device.

According to another aspect of the present disclosure, a system is provided that includes a patient support apparatus, a camera, and an off-board computer. The patient support apparatus includes a support surface adapted to support a patient thereon, a sensor, a transceiver, and a controller. The controller is adapted to instruct the transceiver to transmit a sequence of readings from the sensor to the off-board computer. The camera has a field of view that captures at least a portion of the patient support apparatus and the camera is adapted to generate a video. The off-board computer is adapted to receive the video from the camera and to generate a synchronized data file. The synchronized data file includes a first portion synchronized with a second portion. The first portion contains a visual representation of the sequence of readings from the sensor and the second portion contains the video.

The off-board computer, in some embodiments, is a server in communication with a local area network of a healthcare facility in which the patient support apparatus is located, and the server is adapted to forward the synchronized data file to an electronic device in communication with the local area network.

The electronic device, in some embodiments, is a smart phone assigned to a caregiver.

The camera, in some embodiments, is positioned onboard the patient support apparatus.

The camera, in some embodiments, includes a depth sensor adapted to determine distances to objects appearing within the field of view of the camera.

In some embodiments, the system further includes a second camera positioned onboard the patient support apparatus, and the off-board computer is further adapted to receive a second video from the second camera and to generate a stitched video comprised of a portion of the video from the camera and a portion of the second video from the second camera. In such embodiments, the off-board computer is further adapted to integrate the stitched video into the synchronized data file.

The off-board computer, in some embodiments, is a server adapted to analyze the video to determine a breathing rate of the patient. The server may further be adapted to perform at least one of the following: if the breathing rate exceeds an upper threshold, transmit an alert to a mobile electronic device associated with a caregiver assigned to the patient; or, if the breathing rate is less than a lower threshold, transmit an alert to the mobile electronic device.

In some embodiments, the off-board computer is a server adapted to analyze the video to determine if a ligature is present within the field of view. In such embodiments, the server may further be adapted to transmit a message to a mobile electronic device associated with a caregiver assigned to the patient if the server detects the presence of the ligature.

The off-board computer, in some embodiments, is a server adapted to communicate with a database containing visual characteristics of gowns assigned to patients within a healthcare facility in which the patient support apparatus is positioned. The server, in such embodiments, is adapted to use the visual characteristics to identify within the video a gown worn by the patient.

In some embodiments, the off-board computer is a server adapted to analyze the video to determine a position of the patient's body, to modify a color of the patient's body within the second portion of the synchronized data file, and to transmit the synchronized data file with the modified color of the patient's body to a mobile electronic device associated with a caregiver assigned to the patient. The modified color may comprise shades of a single color, such as, but not limited to, gray.

In some embodiments, the off-board computer is a server adapted to identify the patient support apparatus in the video, to modify the second portion of the synchronized data file by replacing the patient support apparatus with a computer generated rendering of the patient support apparatus, and to transmit the synchronized data file with the computer generated rendering of the patient support apparatus to a mobile electronic device associated with a caregiver assigned to the patient.

The sensor, in some embodiment, includes a load cell of an exit detection system that comprises a plurality of load cells.

The remote control, in some embodiments, is a portable electronic device, such as a smart phone, and the server is adapted to receive a movement command from the remote control and to forward the movement command to the patient support apparatus. The movement command commands the controller of the patient support apparatus to move a component of the patient support apparatus.

In some embodiments, the server is further adapted to analyze the video to determine if any obstruction is present in a movement path of the component, and to forward the movement command to the patient support apparatus only if no obstruction is present in the movement path of the component.

The server, in some embodiments, is further adapted to analyze the video to determine if the patient is present on the support surface of the patient support apparatus, and to forward the movement command to the patient support apparatus only if the patient is not present on the support surface.

The server may be further configured to send a failure message to the remote control if the server does not forward the movement command to the patient support apparatus. The failure message indicates that the component has not been moved.

The server may also, or alternatively, be further configured to send a success message to the remote control if the server does forward the movement command to the patient support apparatus. The success message indicates that the component has been moved.

The server, in some embodiments, is adapted to forward the movement command to the patient support apparatus only if the server is simultaneously streaming the video to the remote control.

The movable component, in some embodiments, is one of an adjustable height litter frame or a Fowler section that is adapted to pivot about a generally horizontal pivot axis.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
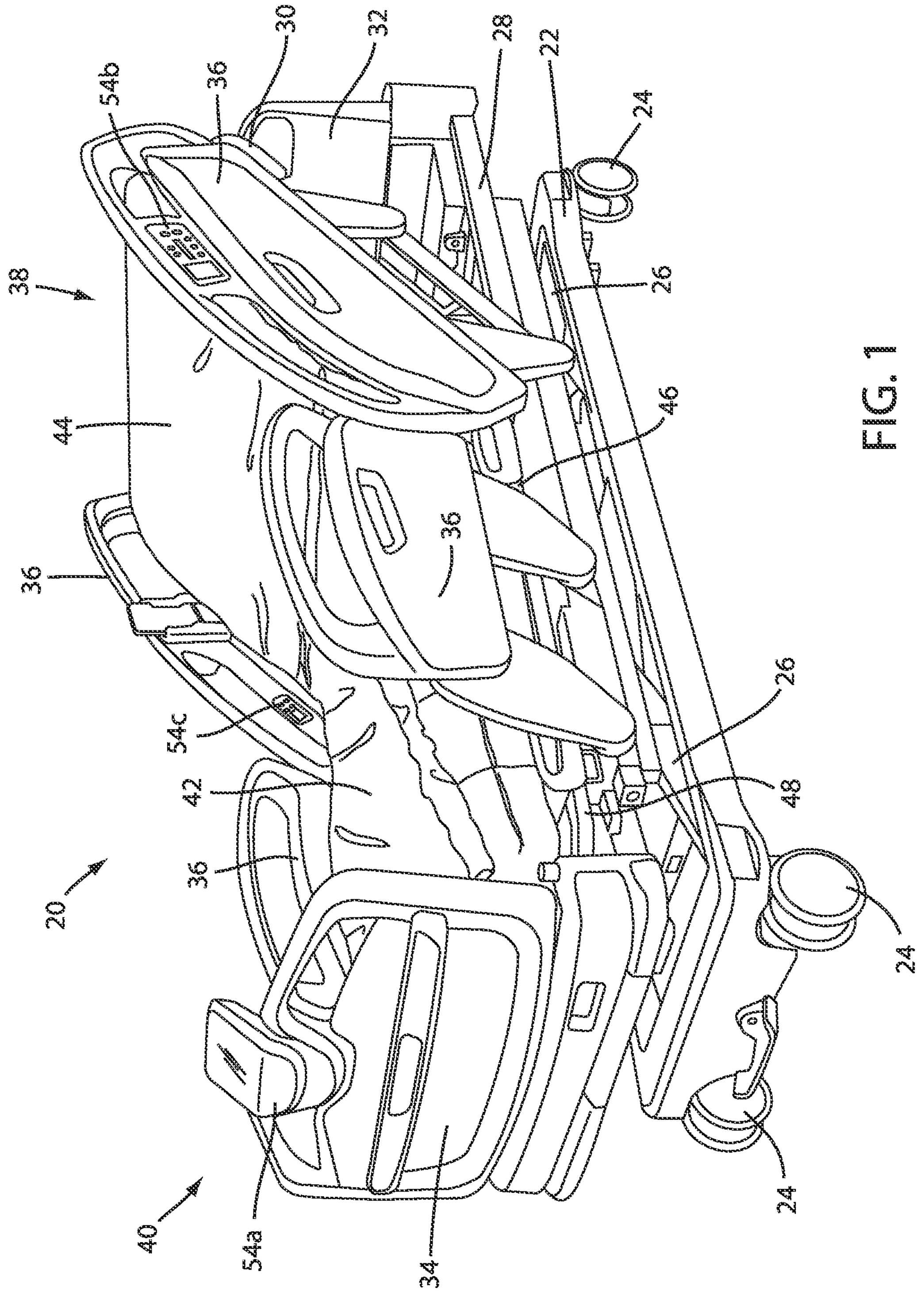
FIG. 1 is a perspective view of one embodiment of a patient support apparatus incorporating various aspects of the present disclosure.

An illustrative patient support apparatus 20 according to a first embodiment of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a recliner, or any other structure capable of supporting a patient in a healthcare environment.

In general, patient support apparatus 20 includes a base 22 having a plurality of wheels 24, a pair of lifts 26 supported on the base 22, a litter frame 28 supported on the lifts 26, and a support deck 30 supported on the litter frame 28. Patient support apparatus 20 further includes a headboard 32, a footboard 34 and a plurality of siderails 36. Siderails 36 are all shown in a raised position in FIG. 1 but are each individually movable to a lower position in which ingress into, and egress out of, patient support apparatus 20 is not obstructed by the lowered siderails 36.

Lifts 26 are adapted to raise and lower litter frame 28 with respect to base 22. Lifts 26 may utilize hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted, to place the litter frame 28 in a flat or horizontal orientation, a Trendelenburg orientation, or a reverse Trendelenburg orientation. That is, litter frame 28 includes a head end 38 and a foot end 40, each of whose height can be independently adjusted by the nearest lift 26. Patient support apparatus 20 is designed so that when an occupant lies thereon, his or her head will be positioned adjacent head end 38 and his or her feet will be positioned adjacent foot end 40. The lifts 26 may be constructed and/or operated in any of the manners disclosed in commonly assigned U.S. patent publication 2017/0246065, filed on Feb. 22, 2017, entitled LIFT ASSEMBLY FOR PATIENT SUPPORT APPARATUS, the complete disclosure of which is hereby incorporated herein by reference. Other manners for constructing and/or operating lifts 26 may, of course, be used.

Litter frame 28 provides a structure for supporting support deck 30, the headboard 32, footboard 34, and siderails 36. Support deck 30 provides a support surface for a mattress 42, or other soft cushion, so that a person may lie and/or sit thereon. The top surface of the mattress 42 or other cushion forms a support surface for the occupant.

Support deck 30 is made of a plurality of sections, some of which are pivotable about generally horizontal pivot axes.

In the embodiment shown in FIG. 1, support deck 30 includes at least a head section 44, a thigh section 46, and a foot section 48, all of which are positioned underneath mattress 42 and which generally form flat surfaces for supporting mattress 42. Head section 44, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

In some embodiments, patient support apparatus 20 may be modified from what is shown to include one or more components adapted to allow the user to extend the width of patient support deck 30, thereby allowing patient support apparatus 20 to accommodate patients of varying sizes. When so modified, the width of deck 30 may be adjusted sideways in any increments, for example between a first or minimum width, a second or intermediate width, and a third or expanded/maximum width.

As used herein, the term "longitudinal" refers to a direction parallel to an axis between the head end 38 and the foot end 40. The terms "transverse" or "lateral" refer to a direction perpendicular to the longitudinal direction and parallel to a surface on which the patient support apparatus 20 rests.

It will be understood by those skilled in the art that patient support apparatus 20 can be designed with other types of mechanical constructions, such as, but not limited to, that described in commonly assigned, U.S. Pat. No. 10,130,536 to Roussy et al., entitled PATIENT SUPPORT USABLE WITH BARIATRIC PATIENTS, the complete disclosure of which is incorporated herein by reference. In another embodiment, the mechanical construction of patient support apparatus 20 may be the same as, or nearly the same as, the mechanical construction of the Model 3002 S3 bed manufactured and sold by Stryker Corporation of Kalamazoo, Michigan. This mechanical construction is described in greater detail in the Stryker Maintenance Manual for the MedSurg Bed, Model 3002 S3, published in 2010 by Stryker Corporation of Kalamazoo, Michigan, the complete disclosure of which is incorporated herein by reference. It will be understood by those skilled in the art that patient support apparatus 20 can be designed with still other types of mechanical constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of patient support apparatus 20 may also take on still other forms different from what is disclosed in the aforementioned references.

Patient support apparatus 20 further includes a plurality of control panels 54 that enable a user of patient support apparatus 20, such as a patient and/or an associated caregiver, to control one or more aspects of patient support apparatus 20. In the embodiment shown in FIG. 1, patient support apparatus 20 includes a footboard control panel **54*a*, a pair of outer siderail control panels 54*b* (only one of which is visible), and a pair of inner siderail control panels 54*c* (only one of which is visible). Footboard control panel 54*a* and outer siderail control panels 54*b* are intended to be used by caregivers, or other authorized personnel, while inner siderail control panels 54*c* are intended to be used by the patient associated with patient support apparatus 20. Each of the control panels 54 includes a plurality of controls 50 (see, e.g. FIGS. 2-3), although each control panel 54** does not necessarily include the same controls and/or functionality.

Among other functions, controls 50 of control panel **54*a* allow a user to control one or more of the following: change a height of support deck 30, raise or lower head section 44, activate and deactivate a brake for wheels 24, arm and disarm an exit detection system, arm and disarm an onboard monitoring system, configure patient support apparatus 20, control one or more cameras and/or camera processing functions, control an onboard scale system, and/or other functions. One or both of the inner siderail control panels 54*c* also include at least one control that enables a patient to call a remotely located nurse (or other caregiver). In addition to the nurse call control, one or both of the inner siderail control panels 54*c* may also include one or more controls for controlling one or more features of a television, room light, and/or reading light positioned within the same room as the patient support apparatus 20. With respect to the television, the features that may be controllable by one or more controls 50 on control panel 54*c* include, but are not limited to, the volume, the channel, the closed-captioning, and/or the power state of the television. With respect to the room and/or night lights, the features that may be controlled by one or more controls 50 on control panel 54*c*** include the on/off state of these lights.

Control panel **54*a* includes a display 52 (FIG. 2) configured to display a plurality of different screens thereon. Display 52 may be a touchscreen-type display, although it will be understood that a non-touchscreen display may alternatively be used. Display 52 displays one or more visual indicators, one or more controls, and/or one or more control screens, and/or other types of information, as will be discussed more below. Display 52 may comprise an LED display, an OLED display, or another type of display. Display 52 is configured to have its brightness level adjusted. That is, the amount of light emitted from display 52 can be varied by a controller included within patient support apparatus 20**, as will be discussed in greater detail below.

Surrounding display 52 are a plurality of navigation controls **50*a-f* that, when activated, cause the display 52 to display different screens on display 52. More specifically, when a user presses navigation control 50*a*, control panel 54*a* displays an exit detection control screen on display 52 that includes one or more icons that, when touched, control an onboard exit detection system. The exit detection system is as adapted to issue an alert when a patient exit from patient support apparatus 20**. Such an exit detection system may include any of the features and functions as, and/or may be constructed in any of the same manners as, the exit detection system disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, the complete disclosure of which is incorporated herein by reference. Other types of exit detection systems can also or alternatively be used.

When a user pressed navigation control **50*b* (FIG. 2), control panel 54 displays a monitoring control screen that includes a plurality of control icons that, when touched, control an onboard monitoring system built into patient support apparatus 20. Further details of one type of monitoring system that may be built into patient support apparatus 20 are disclosed in commonly assigned U.S. patent application Ser. No. 62/864,638 filed Jun. 21, 2019, by inventors Kurosh Nahavandi et al. and entitled PATIENT SUPPORT APPARATUS WITH CAREGIVER REMINDERS, as well as commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosures of both of which are incorporated herein by reference. Other types of monitoring systems can also or alternatively be included with patient support apparatus 20**.

When a user presses navigation control 50*c*, control panel 54*a* displays a scale control screen that includes a plurality of control icons that, when touched, control the scale system of patient support apparatus 20. Such a scale system may include any of the features and functions as, and/or may be constructed in any of the same manners as, the scale systems disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, and U.S. patent application Ser. No. 62/885,954 filed Aug. 13, 2019, by inventors Kurosh Nahavandi et al. and entitled PATIENT SUPPORT APPARATUS WITH EQUIPMENT WEIGHT LOG, the complete disclosures of both of which are incorporated herein by reference. Other types of scale systems can also or alternatively be included with patient support apparatus 20.

When a user presses navigation control 50*d*, control panel 54 displays a motion control screen that includes a plurality of control icons that, when touched, control the movement of various components of patient support apparatus 20, such as, but not limited to, the height of litter frame 28 and the pivoting of head section 44. In some embodiments, the motion control screen displayed on display 52 in response to pressing control 50*d* may be the same as, or similar to, the position control screen 216 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference. In some embodiments, the motion control screen takes on the form of motion control screen 62 shown in FIG. 2. Other types of motion control screens can also or alternatively be included with patient support apparatus 20.

When a user presses navigation control 50*e*, control panel 54*a* displays a motion lock control screen that includes a plurality of control icons that, when touched, control one or more motion lockout functions of patient support apparatus 20. Such a motion lockout screen may include any of the features and functions as, and/or may be constructed in any of the same manners as, the motion lockout features, functions, and constructions disclosed in commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosures of both of which are incorporated herein by reference. Other types of motion lockout control screens can also or alternatively be included with patient support apparatus 20.

When a user presses on navigation control 50*f*, control panel 54*a* displays a menu screen that includes a plurality of menu icons that, when touched, bring up one or more additional screens for controlling and/or viewing one or more other aspects of patient support apparatus 20. Such other aspects include, but are not limited to, diagnostic and/or service information for patient support apparatus 20, mattress control and/or status information, configuration settings, and other settings and/or information. One example of a suitable menu screen is the menu screen 100 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference. Other types of menu screens can also or alternatively be included with patient support apparatus 20.

For all of the navigation controls 50*a-f* (FIG. 2), screens other than the ones specifically mentioned above may be displayed on display 52 in other embodiments of patient support apparatus 20 in response to a user pressing these controls. Thus, it will be understood that the specific screens mentioned above are merely representative of the types of screens that are displayable on display 52 in response to a user pressing on one or more of navigation controls 50*a-f*. It will also be understood that, although navigation controls 50*a-f* have all been illustrated in the accompanying drawings as dedicated controls that are positioned adjacent display 52, any one or more of these controls 50*a-f* could alternatively be touchscreen controls that are displayed at one or more locations on display 52. Still further, although controls 50*a-f* have been shown herein as buttons, it will be understood that any of controls 50*a-f* could also, or alternatively, be switches, dials, or other types of non-button controls.

Control panel 54*a*, in some embodiments, also includes a dashboard 58 (FIG. 2) that communicates the current states of various conditions of patient support apparatus 20 to a caregiver. Dashboard 58 comprises a plurality of icons 60 that are individually illuminated to thereby act as visual indicators for indicating the current state of different conditions of patient support apparatus 20. For example, as shown more clearly with respect to FIG. 2, a first icon 60*a* (e.g., a graphical symbol of an alert over a bed) is backlit by a corresponding light when an exit detection system is armed; a second icon 60*b* (e.g., a graphical symbol of an eye) is backlit by a second light when a monitoring system is armed; a third icon 60*c* (e.g., a graphical symbol of an arrow and bed) is backlit by a third light when litter frame 28 is at its lowest height (or below a threshold height); a fourth icon 60*d* (e.g., a graphical symbol of an unplugged AC power cord) is backlit by a fourth light when the patient support apparatus 20 is plugged into an electrical wall outlet; and a fifth icon 60*e* (e.g., a graphical symbol of a lock and wheel) is backlit by a fifth light when the brake is activated.

The lights positioned behind these icons 60*a-e* may be controlled to be illuminated in different colors, depending upon what state the associated condition is currently in (e.g. the brake is deactivated, exit detection system 82 is disarmed, etc.) and/or one or more of them may alternatively not be illuminated at all when the associated condition is in another state. Additionally, the brightness level of the lights may be adjustable such that, regardless of color, the intensity of the light emitted may be varied by a controller onboard patient support apparatus 20.

Figure 2:
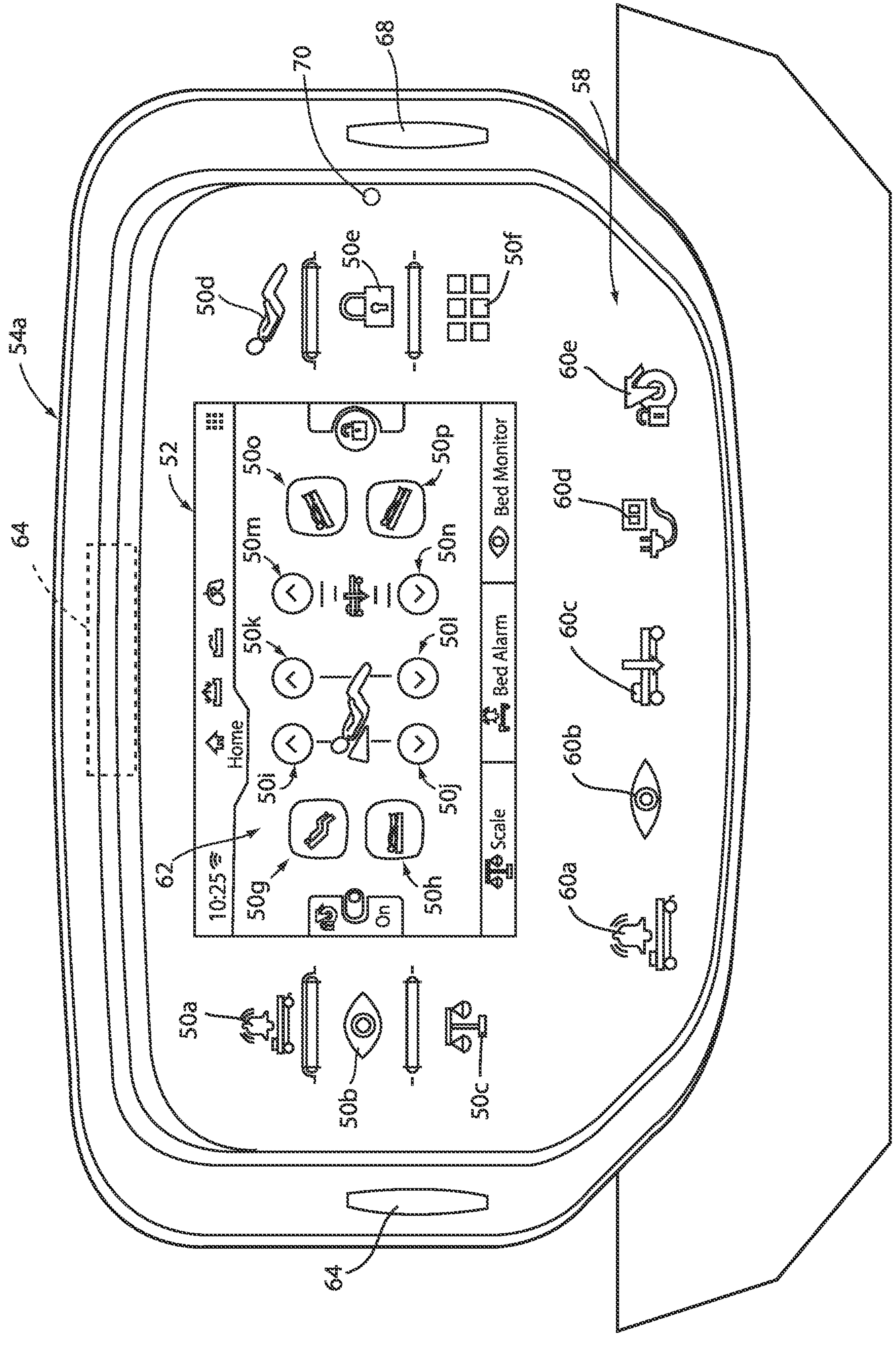
FIG. 2 is a plan view of a footboard control panel of the patient support apparatus of FIG. 1.

Fewer or additional icons 60 may be included as part of dashboard 58 (FIG. 2). The plurality of icons 60 may be dead-fronted on the dashboard 58 of control panel 54*a* such that the plurality of icons 60 are only visible by the caregiver when illuminated by their corresponding icon lights. In some embodiments, dashboard 58 retains the illumination of one or more of icons 60*a-e* at all times. That is, in some embodiments, display 52 is configured to go to sleep (blank)

after a predetermined time period elapses without usage. Dashboard 58, however, retains the illumination of the various icons 60 even after display 52 goes blank, thereby providing the caregiver with information about the status of patient support apparatus 20 when display 52 is blank. Thus, for example, if the brake is not activated and icon 60*e* is illuminated with an amber or red color, this illumination remains for as long as the brake remains inactive, even if display 52 times out and goes to sleep (or otherwise goes blank).

FIG. 2 illustrates one example of a motion control screen 62 that is displayable on display 52 of patient support apparatus 20. Motion control screen 62 is displayed in response to a user navigating to it, such as by pressing on navigation control 50*d*. In some embodiments, motion control screen 62 may be the default screen which is initially displayed on display 52 and/or it may be the screen to which display 52 automatically returns after a predetermined time period of inactivity.

Motion control screen 62 includes a plurality of motion controls 50*g-p* for controlling the movement of patient support apparatus 20. Specifically, it includes a chair control 50*g* for moving patient support apparatus 20 to a chair configuration; a flat control 50*h* for moving patient support apparatus 20 to a flat orientation; a set of Fowler lift and lower controls 50*i* and 50*j*; a set of gatch lift and lower controls 50*k* and 50*l*; a litter frame lift control 50*m*; a litter frame lower control 50*n*; a Trendelenburg control 50*o*; and a reverse Trendelenburg control 50*p*. In some embodiments of patient support apparatus 20, motion control screen 62 are dedicated controls that are separate from display 52.

Control panel 54*a* (FIG. 2) also includes a camera 64 positioned on a back side of control panel 54*a*. Camera 64 is positioned such that its field of view 66 (FIG. 5) encompasses the space above mattress 42 in which a patient is positioned when he or she is sitting or lying on mattress 42. In other words, camera 64 is positioned such that its field of view 66 encompasses the patient whenever the patient is supported on patient support apparatus 20. Although the patient support apparatus 20 shown in FIGS. 1 and 5 only includes a single camera 64, it will be understood that more than one camera 64 may be included on patient support apparatus 20. For example, in the embodiment shown in FIG. 10, patient support apparatus 20 includes nine cameras 64: two of which are positioned on each of the four siderails 36 and another one of which is positioned on the back side of control panel 54*a*. Fewer or greater numbers of cameras 64 may be included on patient support apparatus 20, and the locations of these camera(s) 64 may be changed from those shown in the accompanying drawings.

Each camera 64, in some embodiments, is a camera from the RealSense™ product family D400 series marketed by Intel Corporation of Santa Clara, California. For example, in some embodiments, each camera is an Intel RealSense™ D455 Depth Camera that includes two imagers, an RGB sensor, a depth sensor, an inertial measurement unit, a camera module and a vision processor. Further details regarding this camera are found in the June 2020, (revision 009; document number 337029-009) datasheet entitled "Intel® RealSense™ Product Family D400 Series," published by Intel Corporation of Santa Clara, California, the complete disclosure of which is incorporated herein by reference. Other types of depth cameras marketed by the Intel Corporation, as well as other types of depth cameras marketed by other entities may also, or alternatively, be used according to the teachings of the present disclosure. In some embodiments, cameras may be used that are of the same type(s) as those disclosed in commonly assigned U.S. Pat. No. 1,036,839 issued to Derenne et al. on Jul. 20, 2019, and entitled VIDEO MONITORING SYSTEM, the complete disclosure of which is incorporated herein by reference. As will be discussed in greater detail below, the images captured by camera 64 are utilized by one or more controllers onboard patient support apparatus 20 and/or one or more remote computing devices (e.g. one or more servers) to carry out one or more of the plurality of functions described herein.

Figure 3:
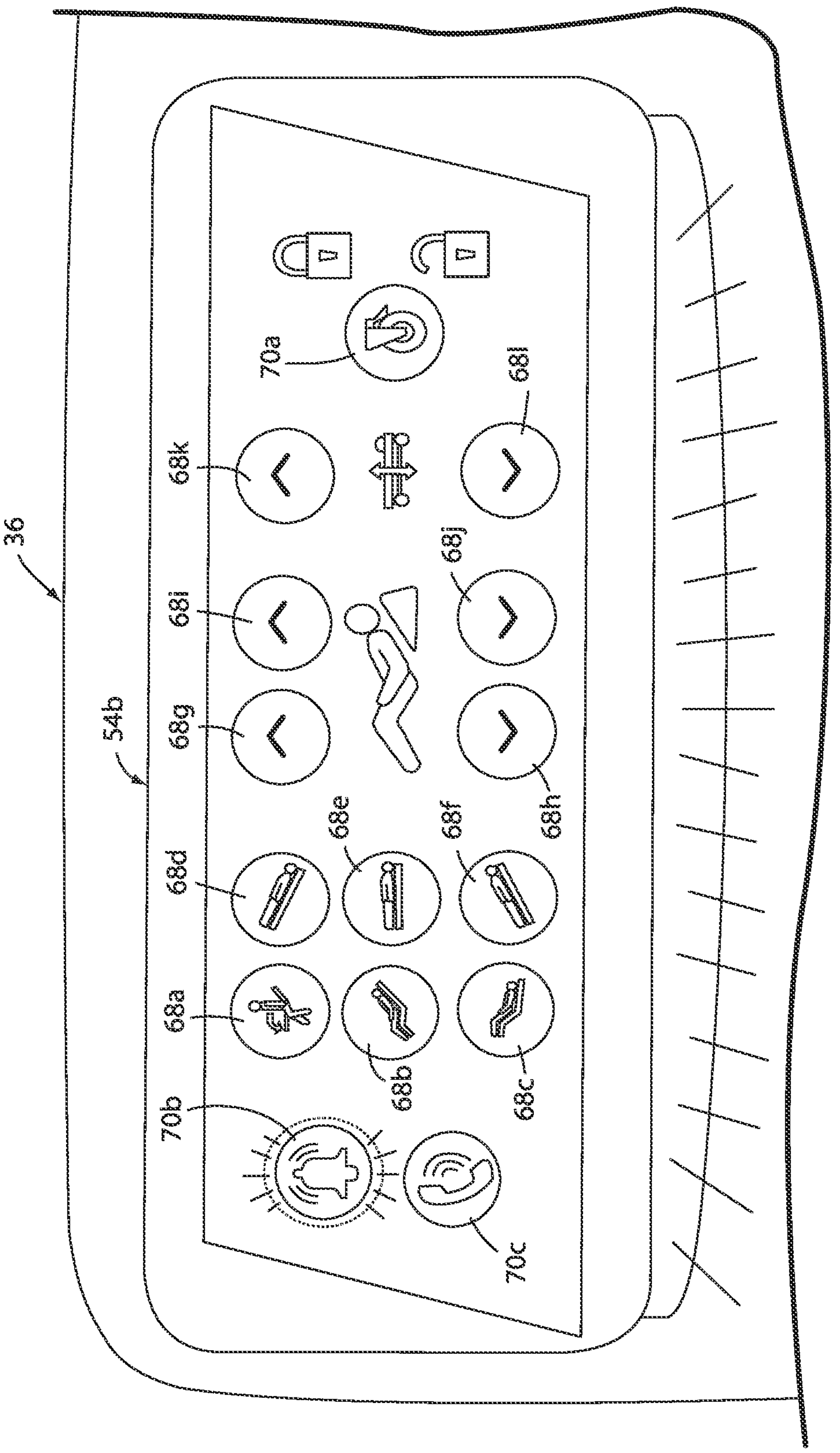
FIG. 3 is a view of a siderail control panel of the patient support apparatus of FIG. 1.

As was noted previously, in some embodiments, additional control panels may be present on the patient support apparatus 20, spaced from control panel 54*a*. FIG. 3 depicts a plan view of one of the control panels 54*b* attached to a head end one of the siderails 36. A similar control panel 54*b* may be located on an opposing head end siderail 36. Control panel 54*b* includes a plurality of controls 68 and one or more visual indicators 70. The controls 68 include a plurality of motion controls 68*a-l* and the indicators 70 include a brake indicator 70*a*, an alarm indicator 70*b*, and a nurse call indicator 70*c*.

Control 68*a* (FIG. 3), when pressed, causes motorized actuators (not shown) aboard patient support apparatus 20 to move litter frame 28 and deck 30 into a patient egress position that allows easier exit for the patient from patient support apparatus 20. The same control 68*a* can also be employed to allow easier ingress into the patient support apparatus 20. Recline control 68*b*, when pressed, causes the motorized actuators to move litter frame 28 and deck 30 to a reclined position, such as shown by the icon in the center of recline control 68*b*. Leg raised control 68*c*, when pressed, causes the motorized actuators to move litter frame 28 and deck 30 such that the legs of the patient are bent and oriented higher than the patient's torso, such as shown by the icon in the center of leg raised control 68*c*.

Trendelenburg control 68*d*, when pressed, causes the motorized actuators to move litter frame 28 and deck 30 to the Trendelenburg position. Flat control 68*e*, when pressed, causes the motorized actuators to move litter frame 28 and deck 30 to a flat orientation. Reverse Trendelenburg control 68*g*, when pressed, causes the motorized actuators to move litter frame 28 and deck 30 to the reverse Trendelenburg position.

Controls 68*g* and 68*h* (FIG. 3) move the gatch portion of the support deck 30 up and down, respectively. Controls 68*g* and 68*h* carry out the same function as controls 50*k* and 50*l* control panel 54*a* (FIG. 2). Controls 68*i* and 68*j* move the Fowler section 44 of support deck 30 up and down, respectively. Controls 68*i* and 68*j* carry out the same function as controls 50*i* and 50*j* control panel 54*a*. Controls 68*k* and 68*l* raise and lower the entire litter frame 28, respectively. Controls 68*k* and 68*l* carry out the same function as controls 50*m* and 50*n* of control panel 54*a*.

Control panel 54*b* also includes indicators 70*a*, 70*b*, and 70*c*. Indicator 70*a* is illuminated in a first manner (e.g. a red or amber light) when a brake onboard patient support apparatus 20 is not activated, and in another manner (e.g. green) when the brake is activated. Indicator 70*b*, in some embodiments, is illuminated in order to remind a caregiver to arm or disarm an exit detection system onboard patient support apparatus 20. In at least one such embodiment, indicator 70*b* emits white light (steady, flashing, or pulsing) when a user presses on egress control 68*a* while the exit detection system is armed, and emits no light at all other times except when the exit detection system is armed and detects a patient exiting from patient support apparatus 20.

When such a patient exit is detected, indicator 70*b* may be activated to emit a red flashing light.

Indicator 70*c* is illuminated when a patient makes a call to a remotely positioned nurse. In some embodiments, indicator 70*c* is illuminated a first color when such a call is placed and illuminated a second color when no such call is placed. In other embodiments, indicator 70*c* is not illuminated when no call is being placed, and is illuminated when such a call is placed.

Figure 4:
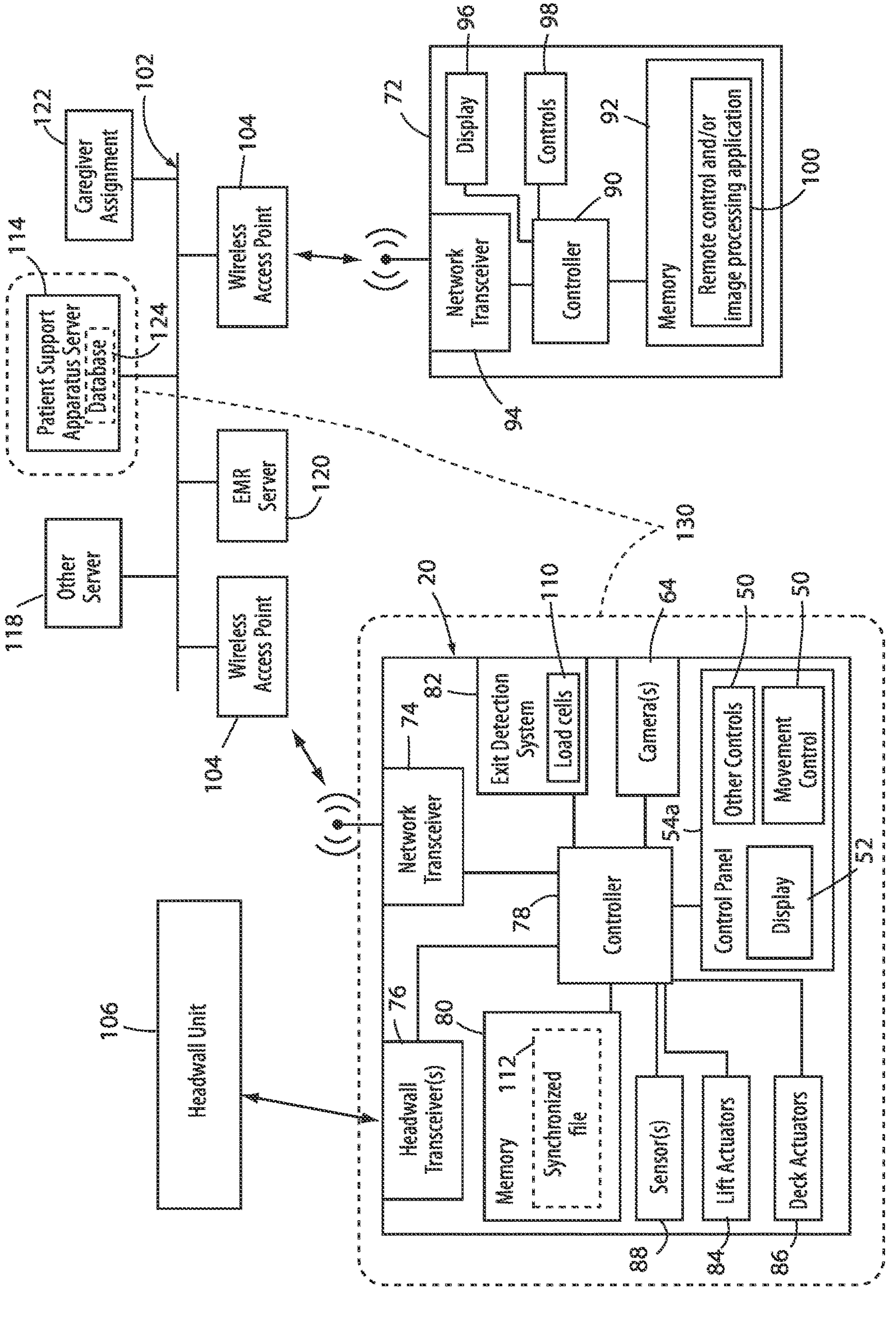
FIG. 4 is a block diagram of the patient support apparatus, an illustrative local area network, and an electronic device in communication with the patient support apparatus via the local area network.

FIG. 4 depicts in more detail the internal components of patient support apparatus 20 and a remote electronic device 72. It will be understood that these components are not necessarily a complete list of components onboard patient support apparatus 20 and/or electronic device 72, and that patient support apparatus 20 and/or electronic device 72 may therefore include additional components beyond those depicted in FIG. 4. Indeed, in some embodiments, patient support apparatus 20 may include any one or more of the components and/or features of any of the patient support apparatuses disclosed in any of the patent references incorporated herein by reference.

As shown in FIG. 4, patient support apparatus 20 includes network transceiver 74, a headwall transceiver 76, a controller 78, a memory 80, control panel 54*a* (as well additional control panels 54*b*, 54*c* which are not shown in FIG. 4), an exit detection system 82, one or more cameras 64, a plurality of lift actuators 84, one or more deck actuators 86, and one or more sensors 88. Each of these components are in communication with each other in one or more conventional manners, such as, but not limited to, one or more the following: a Controller Area Network (CAN); an I-Squared-C bus; a Local Interconnect Network (LIN) bus, Firewire; RS-232; RS-485; Universal Serial Bus (USB); Ethernet; a Serial Peripheral Interface (SPI) bus, and/or in other manners.

Electronic device 72 includes a controller 90, a memory 92, a network transceiver 94, a display 96, and one or more controls 98. Memory 92 includes a software application 100 that is executed by controller 90 and that carries out one or more functions described herein, such as, but not limited to, a remote control function for controlling patient support apparatus 20, an image processing/viewing function for processing and/or viewing images captured by one or more cameras 64, and/or other functions. Electronic device 72 may be a conventional smart phone, tablet computer, laptop computer, or other type of computer that is able to execute software application 100 and that includes the components shown in FIG. 4. Alternatively, electronic device 72 may be a smart television that is adapted to communicate with a computer network and that is adapted to display images received from one or more servers of a local area network 102 of the healthcare facility in which patient support apparatus 20 is positioned.

Controller 78 of patient support apparatus 20 and controller 90 of electronic device 72 may take on a variety of different forms. In the illustrated embodiment (FIG. 4), controllers 78 and 90 are implemented as one or more conventional microcontrollers. However, controllers 78, 90 may be modified to use a variety of other types of circuits-either alone or in combination with one or more microcontrollers-such as, but not limited to, any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controllers 78, 90 when carrying out the functions described herein, as well as the data necessary for carrying out these functions, are stored in corresponding memories 80, 100, respectively, that are accessible to that particular controller 78, 90.

Network transceivers 74 and 94 are, in at least some embodiments, WiFi transceivers (e.g. IEEE 802.11) that wirelessly communicate with each other via one or more conventional wireless access points 104 of the local area network 102 (FIG. 4). In other embodiments, network transceivers 74, 94 may be wireless transceivers that uses conventional 5G technology to communicate directly with each other or indirectly with each other via network 102. In some embodiments, network transceivers 74, 94 may include any of the structures and/or functionality of the communication modules 56 disclosed in commonly assigned U.S. Pat. No. 10,500,401 issued to Michael Hayes and entitled NETWORK COMMUNICATION FOR PATIENT SUPPORT APPARATUSES, the complete disclosure of which is incorporated herein by reference. Still other types of wireless network transceivers may be utilized.

Exit detection system 82 of patient support apparatus 20 (FIG. 4) is adapted to issue an alert when a patient onboard patient support apparatus 20 exits therefrom. Exit detection system 82 may include any of the features and functions as, and/or may be constructed in any of the same manners as, the exit detection system disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, the complete disclosure of which is incorporated herein by reference. In some embodiments, exit detection system 82 includes a plurality of load cells 110 adapted to detect the downward weight exerted by the patient when he or she is positioned on support deck 30. In such embodiments, exit detection system 82 may use the outputs of the load cells to monitor the center of gravity of the patient and issue an alert, when armed, if the patient's center of gravity travels outside of a predefined zone or boundary, such as is explained in greater detail in U.S. Pat. No. 5,276,432 issued to Travis, the complete disclosure of which is incorporated herein by reference. Other types of exit detection systems may be included within patient support apparatus 20.

Headwall transceiver 76 of patient support apparatus 20 (FIG. 4) is adapted to wirelessly communicate with a headwall unit 106. In some embodiments, headwall transceiver 76 includes both an RF (e.g. Bluetooth transceiver) and an infrared transceiver that are used to communication information to and from headwall unit 106, including information that enables the location of patient support apparatus 20 to be determined within the healthcare facility. Headwall transceiver 76, in some embodiments, may include any of the structures, and/or perform any of the functions, of any of the IR transceivers 170 and RF transceivers 172 disclosed in commonly assigned U.S. patent application Ser. No. 63/26, 937 filed May 19, 2020, by inventors Alexander Bodurka et al. and entitled PATIENT SUPPORT APPARATUSES WITH HEADWALL COMMUNICATION, the complete disclosure of which is incorporated herein by reference. In some embodiments, headwall transceiver 76 may be omitted, in which case patient support apparatus 20 is adapted to communicate directly with a communication outlet 108 (FIG. 6) via a nurse call cable and not utilize a headwall unit 106.

Memory 80 of patient support apparatus 20, in addition to including the data and instructions for carrying out the functions described herein, may include a synchronized data file 112. Synchronized data file 112, as will be discussed herein, may be generated by controller 78 synchronizing the outputs of one or more sensors (e.g. sensors 88 or other sensors, such as load cells 110) with a video captured by one or more of the cameras 64. In some embodiments, synchronized file 112 is generated and stored onboard patient support apparatus 20 (e.g. in memory 80). In other embodiments, file 112 may be generated by an off-board computing device (e.g. a server) and stored in another location. In still other embodiments, synchronized data file 112 may be streamed from patient support apparatus 20 (and/or a server of network 102) to one or more remote devices, such as one or more electronic devices 72.

Lift actuators 84 (FIG. 4) drive the lifts 26 up and down. Lift actuators 84 may be hydraulic actuators, electric actuators, or any other suitable powered device for raising and lowering litter frame 28 with respect to base 22. Lift actuators 84 are activated by controller 78 whenever a user activates one or more controls 50 that are control the height of litter frame 28 (e.g. controls 50*m*, 50*n* of FIG. 2 or controls 68*k*, 68*l* of FIG. 3). Deck actuators 86 may also be hydraulic, electric, or some other type of powered actuators. Deck actuators 86 are adapted to pivot one or more of deck sections 44, 46, and/or 48 about a generally horizontal pivot axis. At least one deck actuator 86 is activated by controller 78 whenever a user presses on any of the Fowler controls (e.g. controls 50*i* and 50*j* of FIG. 2 or controls 68*i*, 68*j* of FIG. 3). This deck actuator pivots Fowler section 44 up or down.

Sensor(s) 88 may comprise any of a variety of different sensors that are either positioned onboard patient support apparatus 20 and/or that are positioned elsewhere but in communication with controller 78 (e.g. via transceiver 74). In some embodiments, sensor(s) 88 comprise angle and/or position sensors that determine the angular orientation and/or position of one or more movable components of patient support apparatus 20, such as, but not limited to, litter frame 28 and/or support deck 30. In some embodiments, sensors 88 may comprise any of the sensors 92 disclosed in (including those disclosed in references incorporated therein by reference) commonly assigned U.S. patent application Ser. No. 63/077,864 filed Sep. 14, 2020, by inventors Krishna Bhimavarapu et al. and entitled PATIENT SUPPORT APPARATUS SYSTEMS WITH DYNAMICAL CONTROL ALGORITHMS, the complete disclosure of which is incorporated herein by reference.

Sensors 88 (FIG. 4) may also comprise one or more temperature sensors for sensing the temperature within a room of the healthcare facility, one or more microphones for measuring sounds within the room (ambient noise, patient words or noises, etc.), one or more light sensors for measuring ambient light in the room, one or more thermal sensors for detecting thermal images, and/or one or more vital sign sensors that detect one or more vital signs of the patient(s) assigned to the room, one or more pressure or force sensors positioned on or within the patient support apparatuses 20, or in other locations, that detect the interface pressures experienced by the patient between the patient and the mattress, or still other types of sensors.

In some embodiments, sensors 88 include a pressure sensing mat of the types disclosed in commonly-assigned U.S. Pat. No. 8,161,826 issued to Taylor and/or of the types disclosed in commonly-assigned PCT patent application 2012/122002 filed Mar. 2, 2012 by applicant Stryker Corporation and entitled SENSING SYSTEM FOR PATIENT SUPPORTS, the complete disclosures of both of which are incorporated herein by reference.

In some embodiments, sensors 88 include one or more load cells that are built into one or more patient support apparatuses 20 and that are adapted to detect one or more vital signs of the patient. In at least one of those embodiments, patient support apparatus 20 is constructed in the manner disclosed in commonly-assigned U.S. Pat. No. 7,699,784 issued to Wan Fong et al. and entitled SYSTEM FOR DETECTING AND MONITORING VITAL SIGNS, the complete disclosure of which is hereby incorporated herein by Any of the sensors 88 discussed herein may include one or more load cells, pressure sensors such as piezoelectric and piezoresistive sensors, Hall Effect sensors, capacitive sensors, resonant sensors, thermal sensors, limit switches, gyroscopes, accelerometers, motion sensors, ultrasonic sensors, range sensors, potentiometers, magnetostrictive sensors, electrical current sensors, voltage detectors, and/or any other suitable types of sensors for carrying out their associated functions.

Display 96 and controls 98 of electronic device 72 (FIG. 4) may be conventional structures found on commercially available smart phones, tablet computers, laptop computers, desktop computers, and/or other types of computers. Thus, display 96 may be a conventional LCD screen (either touch sensitive or not), and controls 98 may comprise one or more keys, switches, and/or touch sensitive sensors that are used to control the phone, tablet, or computer. Memory 92 of electronic device 72 includes software application 100 (or multiple software applications 100) that is executed by controller 90 to carry out the imaging functions described herein. Memory 92 may also include additional software, firmware, and/or other data used for carrying out the functions described herein. Memory 92, as with memory 80, may be conventional flash memory, one or more hard drives, and/or any other type of nonvolatile memory that is accessible by the respective controller 78, 90.

Patient support apparatus 20 is configured to communicate with one or more servers on local area network 102 of the healthcare facility (FIG. 4). One such server is a patient support apparatus server 114. Patient support apparatus server 114 is adapted, in at least one embodiment, to receive status information from patient support apparatuses 20 positioned within the healthcare facility and distribute this status information to caregivers, other servers, and/or other software applications. In some embodiments, patient support apparatus server 114 is configured to communicate at least some of the status data received from patient support apparatuses 20 to a remote server 116 (FIG. 6) that is positioned geographically remotely from the healthcare facility. Such communication may take place via a network appliance 146 (FIG. 6), such as, but not limited to, a router and/or a gateway, that is coupled to the Internet 148. The remote server 116, in turn, is also coupled to the Internet 148, and patient support apparatus server 114 is provided with the URL and/or other information necessary to communicate with remote server 116 via the Internet connection between network 102 and server 116.

Local area network 102 is also configured to allow one or more electronic devices 72 and patient support apparatuses 20 to access the local area network 102 via wireless access points 104. It will be understood that the architecture and content of local area network 102 will vary from healthcare facility to healthcare facility, and that the example shown in FIG. 4 is merely one example of the type of network a healthcare facility may be employ. Typically, additional servers, such as an ADT server 118, an EMR server 120, a caregiver assignment server 122, and still other servers (discussed below with respect to FIG. 6) will be hosted on network 102 and one or more of them may be adapted to communicate with patient support apparatus server 114.

Figure 6:
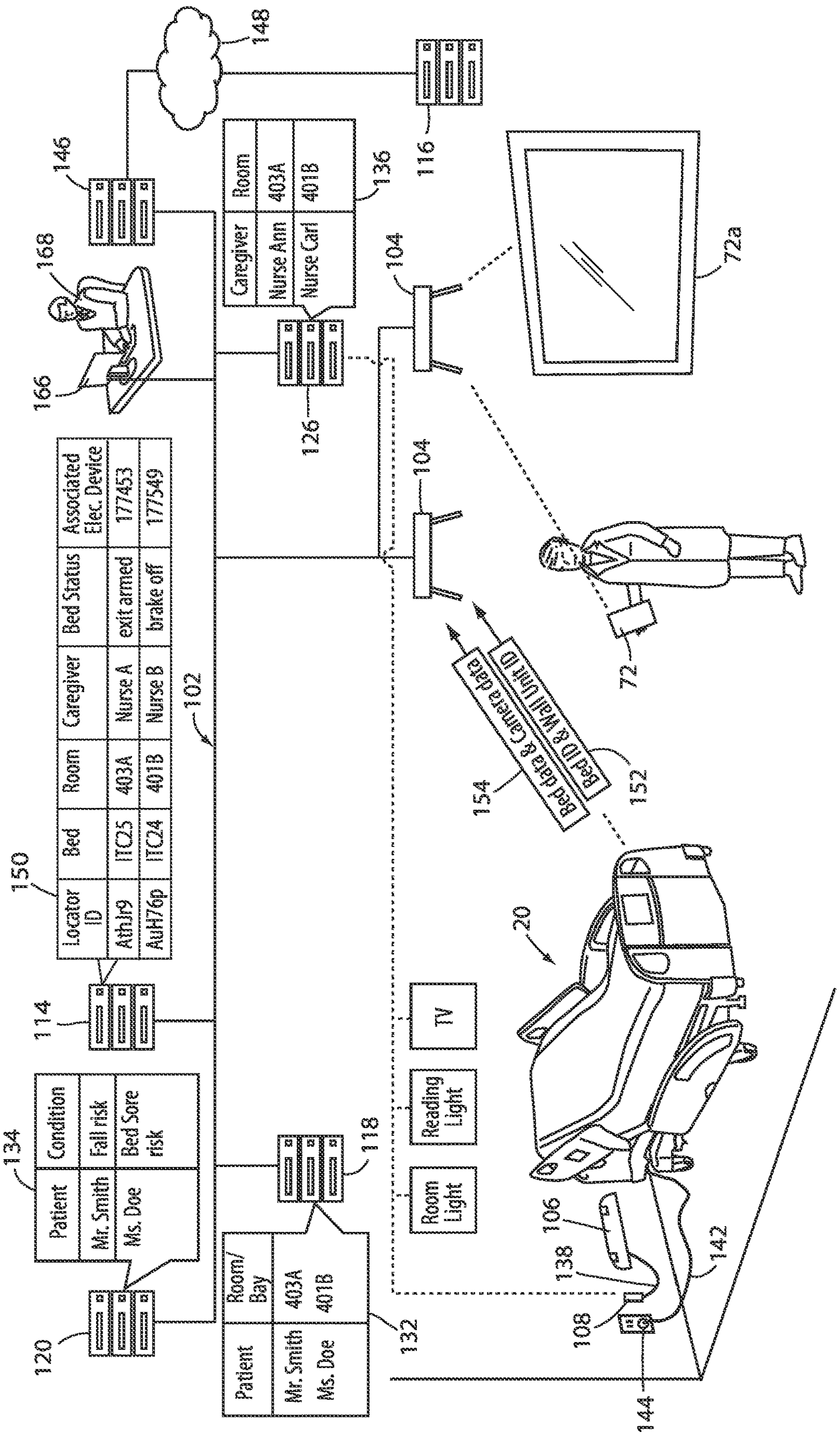
FIG. 6 is a diagram of a vision system and includes the patient support apparatus, the local area network, and a plurality of electronic devices in communication with the patient support apparatus.

The combination of patient support apparatus server 114 and patient support apparatus 20 form a vision system 130 that, as will be discussed in greater detail below, is adapted to perform one or more functions related to the images gathered by camera(s) 64. It will be understood that vision system 130 may, in some embodiments, include additional cameras 64 that are not positioned on patient support apparatus 20, and that vision system 130 may also, or alternatively, include one or more other servers, such as a remote server 116 (FIG. 6). Still further, in some embodiments, vision system 130 may include one or more patient support apparatuses 20 that have more than a single camera 64 positioned thereon.

In some embodiments, each video camera 64 has its own processor integrated therein that is adapted to partially or wholly process the images captured by the image sensor(s) of the camera 64. For example, when using an Intel D400 series camera as camera 64, these cameras include an Intel RealSense Vision Processor D4, along with other electronic circuitry, that performs various vision processing on the signals captured by the various sensors that are part of the D400 series of cameras. For purposes of the following description, the use of the term "outputs," "signals," "image signals," or the like from cameras 64 will refer to either unprocessed image data captured by the camera 64, or partially or wholly processed image data that is captured by cameras 64 and partially or wholly processed by the processor integrated into the camera 64.

Controller 78 of patient support apparatus 20 (FIG. 4) is adapted to receive the outputs from camera 64 and perform additional processing on these outputs and/or to forward the camera outputs to patient support apparatus server 114 via network transceiver 74's connection to a wireless access point 104. Patient support apparatus server 114, in turn, is adapted to either perform yet additional processing on these outputs and/or to forward some or all of these outputs to one or more electronic devices 72 that are in communication with server 114 (e.g. via a wireless access point 104 and the electronic device's network transceiver 94). It will be understood that the distribution of labor in the additional processing of the outputs of cameras 64 between controller 78 and server 114 may be varied in different embodiments of vision system 130. That is, in some embodiments, controller 78 may do all of the processing of the outputs from cameras 64 and merely send the results of that processing to server 114. Alternatively, in some embodiments, the outputs from cameras 64 may be forwarded to server 114 without any additional processing by controller 78 and server 114 may then perform all of the additional processing of those outputs. Still further, the additional processing of outputs from cameras 64 may be shared in any fashion between controller 78 and server 114.

As was noted above, the precise number and location of cameras 64 on patient support apparatus 20 (and/or elsewhere) may vary, depending upon the data that is intended to be captured by the cameras 64 in a particular embodiment of vision system 130. Each camera 64 may be either mounted in a fixed orientation, or it may be coupled to a mounting structure that allows the orientation of the camera to be automatically adjusted by controller 78 and/or server 114 such that the camera may record images of different areas of the room by adjusting its orientation. Still further, each camera 64 may include zoom features that allow controller 78 and/or server 114, or another intelligent device, to control the zooming in and zooming out of the cameras 64 such that both close-up images and wider field of view images may be recorded, as desired.

Server 114 (FIG. 4) either includes a database 124, or is adapted to communicate with a separate database 124. Regardless of whether database 124 is part of, or separate from, server 114, database 124 contains data that is used by server 114 and/or controller 78 in carrying out one or more of the functions described herein. Such data may include, but is not necessarily limited to, any of the following: sheet/gown attribute data, restrain attribute data, patient support apparatus attribute data, camera location information, patient support apparatus movement capabilities, and association data.

The sheet/gown attribute data refers to color, patterns, and/or other visual information regarding the sheets and/or gowns that are used in a particular healthcare setting. Generally speaking, specific healthcare facilities use gowns for patients that are of the same color and/or pattern. Alternatively, they may use several different types of gowns that each have their own color and/or patterns on them. Similarly, the sheets used on patient beds may be of the same color and/or have the same pattern, or the healthcare facility may use a set of colors and/or patterns for its patient support apparatuses. Regardless of whether or not a healthcare facility uses only a single type, or multiple types, of gowns and/or sheets, the color and/or pattern attributes of these items are stored in database 124 in at least one embodiment. As will be discussed in greater detail below, vision system 130 uses this color and/or pattern information to identify the sheets and/or gowns that are captured in the images of cameras 64. By identifying the sheets and/or gowns, vision system 130 is better able to distinguish the patient and/or the sheets in the image from other objects that are captured in the images.

The restrain attribute data refers to color, patterns, and/or other visual information regarding any patient restraints that may be used by a particular healthcare facility for restraining a patient while positioned on patient support apparatus 20. Such restraints may be used for certain types of patients that are determined to be of potential danger to themselves and/or to others. Such restraints restrain the patient from getting out of patient support apparatus 20 and/or restrain movement of their arms, legs, neck, and/or other body parts. Vision system 130 is configured to allow authorized users to enter into database 124 attribute data defining the color, pattern, position, shape, and/or other visual characteristics of the restraints that they use within their particular healthcare facility. Vision system 130 then uses this attribute data to recognize the restraints in the images it captures. In at least one embodiment, vision system 130 is configured to issue an alert to one or more caregivers if one or more cameras 64 detect that a restraint is not applied to a patient. That is, vision system 130 uses the restraint attribute data to determine whether one or more restrains have been applied to the patient and, if not, it may be configured to issue an alert to caregivers alerting them of the fact that one or more restraints have not been applied.

The patient support apparatus attribute data stored in database 124 (FIG. 4) refers to the color, size, shape, and/or other data that assists vision system 130 (controller 78 and/or server 114) in identifying components and/or portions of patient support apparatus 20 that show up in the images captured by cameras 64. Such attribute data may assist vision system 130 in identifying the siderails 36 of the bed, the head or Fowler section 44 of the bed, the mattress 42, the headboard 32, the footboard 34, the control panels 54 on the bed, and/or other components of the bed that may be positioned within the field of view of one or more of the cameras 64. In some embodiments, vision system 130 may be configured to issue an alert if headboard 32 and/or footboard 34 are missing and/or removed from patient support apparatus 20, as determined from analysis of the images captured by one or more cameras 64.

The camera location information stored in database 124 (FIG. 4) refers to the location of each camera 64 on patient support apparatus 20. When multiple cameras 64 are positioned onboard patient support apparatus 20, the location of each camera 64 relative to each other may be stored in database 124 and used, in some embodiments, for stitching together separate image data from multiple cameras 64 into a single, stitched image. Such location information may also be used for other purposes.

The patient support apparatus movement abilities refer to the components of patient support apparatus 20 that are physically movable, as well as where those components are located on the patient support apparatus 20 and their range of motion. As will be discussed in greater detail below, server 114 and/or controller 78 may be adapted to allow a person to remotely control movement of one or more components of patient support apparatus 20 if an analysis of the concurrent images captured by camera(s) 64 indicate that there are no obstacles in the movement path of that component. In order to determine if any such obstacles are present or not, server 114 and/or controller 78 utilize this data so that they are able to identify the movement path of the component in the captured images and to analyze the captured images to determine if an obstacle exists in the movement path.

The association data that may be stored in database 124 is data that associates the location of a particular patient support apparatus 20 to a particular room (and/or bay within a room) within the healthcare facility, the association of particular rooms and/or bays with particular caregivers, and/or the association of particular rooms and/or bays with particular electronic devices 72 that are to receive data regarding particular patient support apparatuses 20, or that are to send data regarding particular patient support apparatuses 20.

In some embodiments, database 124 includes a table of data that server 114 consults to determine the corresponding data it is to use for a particular patient support apparatus 20 based on an ID, or other indicator, that it receives from the patient support apparatus 20. For example, in some embodiments, patient support apparatus 20 sends an ID to server 114 via transceiver 74 that indicates the type of patient support apparatus that it is. From this ID, server 114 may consult a table of different types of patient support apparatuses 20 that contains data for each type. The data may indicate any of the previously discussed data, such as the movement capabilities of the patient support apparatus, the shape and/or color of the patient support apparatus, the location of the camera(s) onboard the patient support apparatus 20, and/or other information. Thus, for example, if patient support apparatus 20 sends an ID to server 114 that identifies patient support apparatus 20 as a type A patient support apparatus 20, server 114 may be configured to consult a table that indicates that type A patient support apparatuses 20 have three cameras located at specific locations, are able to have their Fowler sections 44 pivoted upwardly 80 degrees, can have their litter frames raised/lowered fifteen inches, etc.

Figure 5:
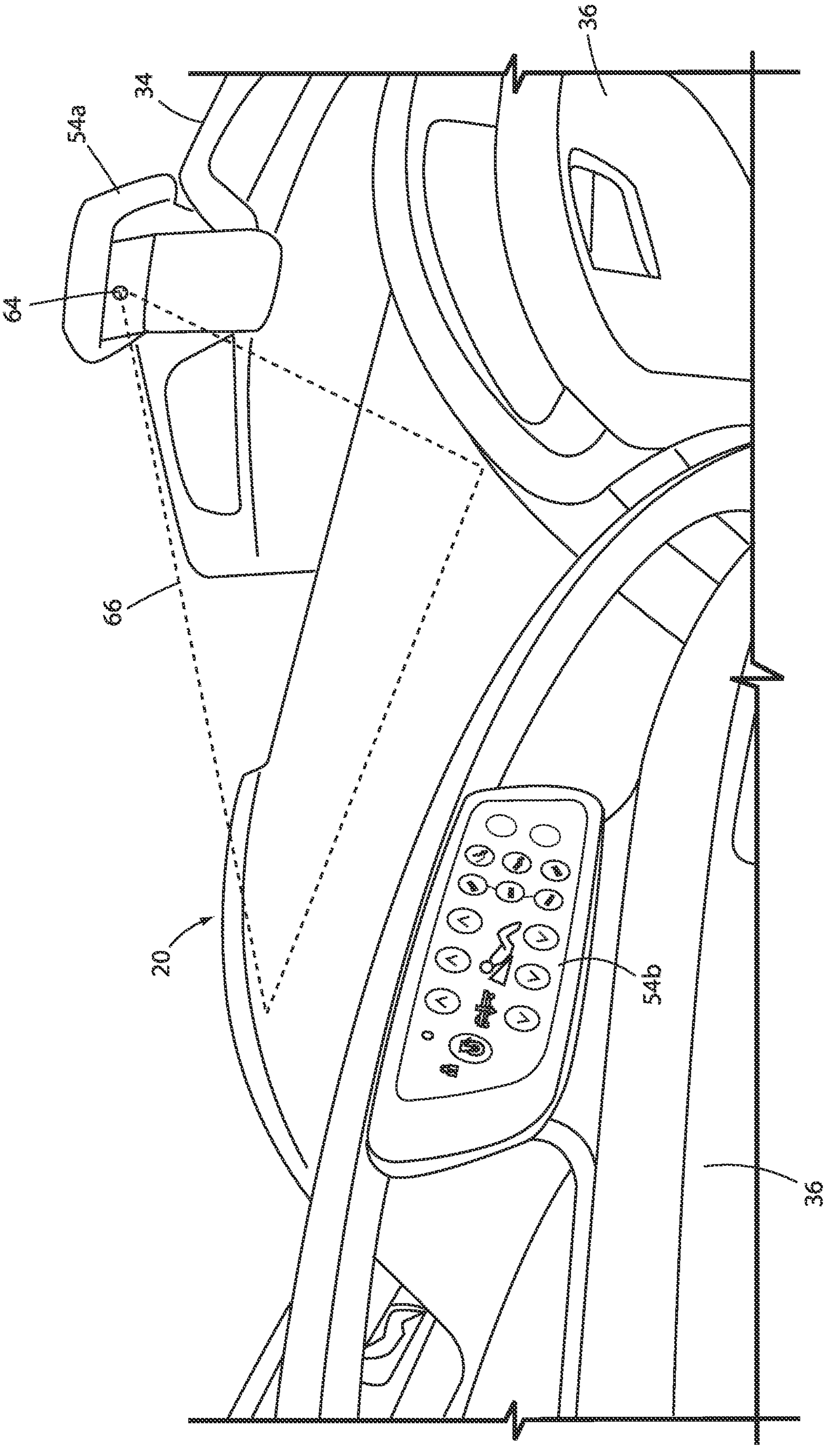
FIG. 5 is a perspective view of an underside of the footboard control panel showing an onboard camera and an illustrative field of view of the camera.

FIG. 5 illustrates one suitable location for camera 64 on patient support apparatus 20. As can be seen therein, camera 64 is positioned on a rear side of footboard control panel 54*a* and is aimed such that its field of view captures substantially all of the volume of space that a patient may occupy when he or she is sitting or lying on mattress 42. In other words, field of view 66 is large enough such that substantially all of the patient will be within the field of view 66 whenever he or she is sitting or lying on mattress 42. As was noted previously, the images captures by camera 64 are processed and/or forwarded by controller 78 to server 114. Either or both of these two structures (controller 78 and/or server 114) include software components that are adapted to carry out the image analysis and processing functions described herein.

In some embodiments, either or both of controller 78 and server 114 include commercially available software that is adapted to carry out the image analysis discussed herein. For example, in some embodiments, either controller 78 and/or server 114 include the commercially available software suite referred to as OpenCV (Open Source Computer Vision Library), which is an open source computer vision library supported by Willow Garage of Menlo Park, California. The OpenCV library has been released under the Berkeley Software Distribution (BSD) open source license. The OpenCV library has more than 2500 computer vision algorithms and is available for use with various commercially available operating systems, including Microsoft Windows, Linux/Mac, and iOS. The OpenCV algorithms include a comprehensive set of both classic and state-of-the-art computer vision and machine learning algorithms. These algorithms are designed to be used to detect and recognize faces, identify objects, classify human actions in videos, track camera movements, track moving objects, extract 3D models of objects, produce 3D point clouds from stereo cameras, stitch images together to produce high resolution images of entire scenes, find similar images from an image database, follow eye movements, recognize scenery and establish markers to overlay scenery with augmented reality, and other tasks.

The OpenCV library has to date included multiple major releases (version 4.5.2 was released in 2021), and any one of these major versions (as well as any of the multiple intermediate versions), is suitable for carrying out the features and functions described in more detail herein. In at least one embodiment of patient support apparatus 20 and/or server 114, customized software is added to interact with and utilize various of the software algorithms of the OpenCV library in order to carry out the features described herein. Other commercially available software may also be used, either in addition to or in lieu of the OpenCV library.

FIG. 6 illustrates in greater detail one manner of implementing vision system 130 within the existing infrastructure of a healthcare facility. FIG. 6 is similar to FIG. 4 but shows more detail regarding the servers that are present on local area network 102, and shows the exteriors or patient support apparatus 20 and electronic devices 72, rather than the interior components (such as is shown in FIG. 4). Local area network 102 includes a conventional Admission, Discharge and Tracking (ADT) server 118, a conventional Electronic Medical Records server 120, a conventional nurse call system server 126 (which may carry out the same function as caregiver-assignment server 122), and patient support apparatus server 114, and a plurality of conventional wireless access points 104.

ADT server 118 stores patient information, including the identity of patients and the corresponding rooms and/or bays within rooms to which the patients are assigned. That is, ADT server 118 includes a patient-room assignment table 132, or functional equivalent to such a table. The patient-room assignment table 132 correlates rooms, as well as bays within multi-patient rooms, to the names of individual patients within the healthcare facility. The patient's names are entered into the ADT server 118 by one or more healthcare facility staff whenever a patient checks into the healthcare facility and the patient is assigned to a particular room within the healthcare facility. If and/or when a patient is transferred to a different room and/or discharged from the healthcare facility, the staff of the healthcare facility update ADT server 118. ADT server therefore maintains an up-to-date table 132 that correlates patient names with their assigned rooms.

EMR server 120 (FIG. 6) stores individual patient records. Such patient records identify a patient by name and the medical information associated with that patient. Such medical information may include all of the medical information generated from the patient's current stay in the healthcare facility as well as medical information from previous visits. EMR table 134 shows an abbreviated example of two types of medical information entries that are commonly found within a patient's medical records: a fall risk entry indicating whether the patient is a fall risk, and a bed sore risk entry indicating whether the patient is at risk for developing bed sores. As noted, EMR server 120 includes far more additional information in the medical records of each patient than what is shown in table 134 of FIG. 6. It will be understood that the term "EMR server," as used herein, also includes Electronic Health Records servers, or EHR servers for short, and that the present disclosure does not distinguish between electronic medical records and electronic health records.

Nurse call server 126 is shown in FIG. 6 to include a caregiver assignment table 136 that matches caregivers to specific rooms and/or bays within the healthcare facility. Although table 136 only shows caregivers assigned to a single room, it will be understood that each caregiver is typically assigned to multiple rooms. In some nurse call systems, caregivers are assigned to specific patients, rather than to specific rooms, in which case table 136 may correlate caregivers to individual patients rather than rooms.

Nurse call system server 126 is configured to communicate with caregivers and patients. That is, whenever a patient on a patient support apparatus 20 presses, or otherwise activates, a nurse call, the nurse call signal is transmitted wirelessly from headwall transceiver 76 to headwall unit 106, which in turn forwards the signals to communication outlet 108 via a nurse call cable 138. The communication outlet 108 forwards the signals to nurse call server 126 via one or more conductors 140 (and/or through other means). The nurse is thereby able to communicate with the patient from a remote location. In some embodiments, patient support apparatus 20 is not adapted to wirelessly communicate with outlet 108, but instead communicates with communication outlet 108 via a direct coupling of nurse call cable 138 between patient support apparatus 20 and outlet 108. In those embodiments of patient support apparatus 20 that are adapted to wirelessly communicate with outlet 108, headwall unit 106 may take on any of the forms and/or functionality of any of the headwall units disclosed in commonly assigned U.S. patent application Ser. No. 63/193,778 filed May 27, 2021, by inventors Krishna Bhimavarapu et al. and entitled PATIENT SUPPORT APPARATUS AND HEADWALL UNIT SYNCING, and/or any of the headwall units that are disclosed in any of the patent references incorporated therein by reference. The complete disclosure of the aforementioned 63/193,778 patent application, as well as all of the references incorporated therein by reference, are hereby incorporated herein by reference in their entirety.

Power to the patient support apparatus 20 is provided by an external power source and/or an onboard battery. As shown in FIG. 6, patient support apparatus 20 may include an alternating current (A/C) power cord 142 that is plugged into a conventional electrical wall outlet 144 to provide power to patient support apparatus 20 from an external power source.

Local area network 102 may include additional structures not shown in FIG. 6, such as, but not limited to, one or more conventional work flow servers and/or charting servers that monitor and/or schedule patient-related tasks for particular caregivers, and/or still other types of servers.

Patient support apparatus server 114 includes a table 150 (FIG. 6) that correlates specific location identifiers to specific patient support apparatuses 20, as well as to specific rooms, caregivers, status information, and electronic devices 72. Patient support apparatus server 114 determines the location of each patient support apparatus 20 within the healthcare facility by receiving one or more messages 152 from patient support apparatuses that correlate a unique patient support apparatus ID with a unique ID from the adjacent headwall unit 106. In other words, when patient support apparatus 20 establishes communication with a headwall unit 106, that headwall unit forwards its headwall ID to patient support apparatus 20 (via a transceiver that communicates with transceiver 76). The patient support apparatus 20 receives the unique ID of its adjacent headwall unit 106 and then forwards its own ID and the headwall unit 106's ID in one or more messages 152 to network 102. Messages 152 are directed to patient support apparatus server 114.

In addition to sending messages 152, patient support apparatuses 20 are further adapted send data messages 154 to network 102 via network transceiver 74. The data messages 154 contain data about the status of patient support apparatus 20 and/or visual image data from one or more cameras 64 positioned onboard the patient support apparatus 20. The visual image data may include live (or delayed) streaming video images, non-streamed videos, portions of videos, and/or any other data related to the images captured by cameras 64.

The data about the status of patient support apparatus 20 contained within messages 154 may also include any other information that is generated by patient support apparatus 20, such as, but not limited to, the status of any of its siderails 36, its brake, the height of litter frame 28, the state of its exit detections system 82, and/or any other data. Although FIG. 6 only illustrates messages being sent off of patient support apparatus 20 to network 102, it will be understood that server 114 is also capable of sending data to patient support apparatus 20. Communication between patient support apparatuses 20 and server 114 is therefore bidirectional.

In some embodiments, server 114 is configured to share the patient support apparatus data (including visual data) that is receives (via messages 154) with only caregivers who are responsible for the patient associated with the particular patient support apparatus 20 that the message 154 originated from. In other words, in some embodiments, server 114 is configured to forward data to only a subset of the electronic devices 72, and that subset is chosen based on the caregivers who are responsible for a particular patient. In this manner, for example, a caregiver who is assigned to patients A-G will not receive data on his or her associated electronic device 72 (e.g. smart phone) from patient support apparatuses that are assigned to patients H-Z.

Server 114 may be configured to determine which electronic devices 72 to transmit patient support apparatus data to based on information contained within table 150, which may be generated by server 114 in response to communication with other servers. Specifically, once server 115 knows the room (and/or bay) that the status data pertains to, it can correlate this room with a particular patient by consulting ADT server 118 and/or nurse call server 126 (or another server on network 102) that correlates rooms to specific caregivers. Once the specific caregiver is identified, server 114 is further configured to maintain, or have access to, a list that identifies which electronic devices 72 are associated with which caregivers. Messages can then be sent by server 114 to only the appropriate caregiver's electronic devices 72.

As shown in FIG. 6, some electronic devices, such as electronic device 72*a*, are communal electronic devices that are intended to be viewed by multiple caregivers, such as all caregivers that are assigned to a particular wing, department, unit, or some other segment of the healthcare facility. When the healthcare facility includes such communal electronic devices 72*a*, server 114 is programmed with, or is programmed to have access to, data that lists the rooms that are associated with each such communal electronic device 72*a*. Thus, for example, a first communal electronic device 72*a* may be intended to display data for rooms 400 through 440, while a second communal electronic device 72*a* may be intended to display data for rooms 450 through 490. In such a case, server 114 is informed of the room assignments for each communal electronic device 72*a* and thus only sends patient support apparatus data from a particular room to the communal electronic device(s) 72*a* that are intended to display data for that particular room.

Server 114 includes a table (not shown), or has access to a table, that contains the surveying data performed when headwall units 106 were installed within the healthcare facility, and which correlates the specific headwall unit IDs with specific locations within the healthcare facility. Server 114 may use this data to determine which room and/or bay a particular patient support apparatus 20 is currently located in after it receives a message 152 from that particular patient support apparatus 20.

In any of the embodiments disclosed herein, server 114 may be configured to additionally execute a caregiver assistance software application of the type described in the following commonly assigned patent applications: U.S. patent application Ser. No. 62/826,097, filed Mar. 29, 2019 by inventors Thomas Durlach et al. and entitled PATIENT CARE SYSTEM; U.S. patent application Ser. No. 16/832,760 filed Mar. 27, 2020, by inventors Thomas Durlach et al. and entitled PATIENT CARE SYSTEM; and/or PCT patent application serial number PCT/US2020/039587 filed Jun. 25, 2020, by inventors Thomas Durlach et al. and entitled CAREGIVER ASSISTANCE SYSTEM, the complete disclosures of which are all incorporated herein by reference.

Figure 7:
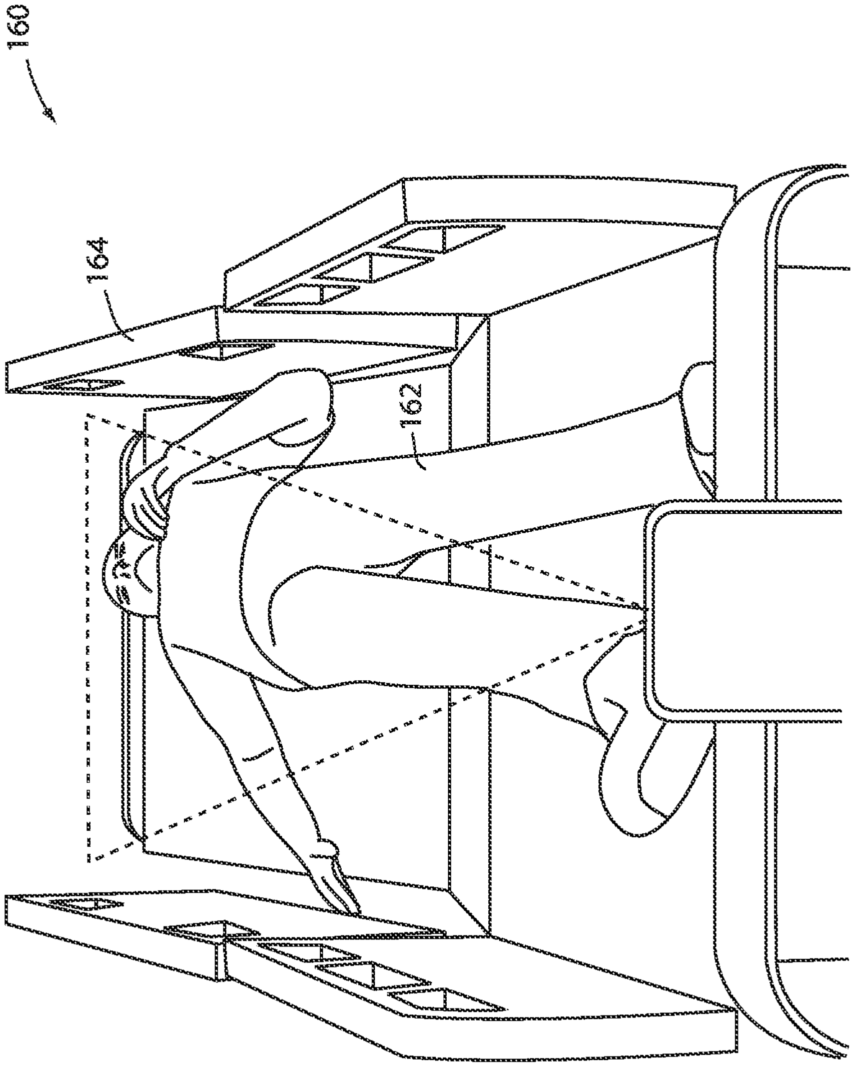
FIG. 7 is a perspective view rendering of the patient support apparatus and a patient positioned thereon that may be generated from images captured from one or more cameras.

FIG. 7 illustrates one manner in which the images output from one or more cameras 64 may be processed by vision system 130 and displayed to one or more authorized individuals. Such display may take play via one or more of the displays 52 on patient support apparatus, one or more of the displays 96 of the electronic devices 72, and/or any other computing device with a display that is in communication with server 114. FIG. 7 illustrates a processed image 160 from a video captured by one or more cameras 64. The processed image 160 is only one frame of a sequence of frames that form a video that corresponds to the video captured by the one or more cameras.

Processed image 160 depicts a patient rendering 162 and a patient support apparatus rendering 164. The patient rendering 162 is generated by controller 78 and/or server 114 by analyzing the video images from one or more camera 64 to identify the position of the patient's body within those video images. Once the patient's body is identified, controller 78 and/or server 114 modify the images of the patient's body within the video images in one or more manners. Such modifications include modifications to the color of the patient's body and/or, in some embodiments, modifications to the face and/or other identifying characteristics of the patient. For example, in the example illustrated in FIG. 7, controller 78 and/or server 114 has modified the color of the patient's body in the video images to be comprised of shades of a single color (gray). In other words, all of the portions of the patient's body within these images has been modified to have a gray color. It will, of course, be understood that other colors besides gray may be used as the primary color for rendering the patient's body within processed image 160.

It will also be understood that, in some embodiments, the patient's body is modified in one or more other manners, such as the size and/or shape of the patient's body. For example, in some embodiments, controller 78 and/or server 114 is configured to replace one or more of the patient's body parts within the captured images with generic renderings of those same body parts in order to better conceal the patient's identity, such as the patient's head, arms, legs, torso, feet, fingers, etc. Thus, as one example, the image of the patient's body captured by camera(s) 64 may include all of the image details captured by the camera(s) 64 with the exception of the patient's head, which may be replaced with a generic rendering 162 of a human head, thereby anonymizing the patient shown in processed image 160. As another example, the image of the patient's torso that is captured by camera(s) 64 may be replaced by a generic rendering 162 of a human torso, thereby providing another layer of anonymization to the patient's identity. Still other partial or whole renderings 162 of the patient's body may be performed.

It will be understood that the renderings of the patient's body 162 (FIG. 7) are done in the same general location within the images that the patient's actual body appears. Therefore, as the patient's body moves within the video captured by camera(s) 64, controller 78 and/or server 114 will move the renderings of the portions (or all) of the patient's body within the processed images 160. As a result, when controller 78 and/or server 114 display the processed images 160 on a display, the portions of the patient's body that are rendered will be rendered such that they move in a manner that generally matches the movement of the patient's actual body. For example, if the patient turns his or her head within the video captured by camera 64 and vision system 130 is configured to replace the patient's head with a rendering of a human head, controller 78 and/or server 114 are configured to render the human head within the processed video images 160 such that is too turns in the same general direction as the patient's head actually turns. In other words, the renderings of the patient's body, whether partial or whole, are generated by controller 78 and/or server 114 in such a manner that they match or track the movement of the patient's actual body. In this manner, the viewer of processed images 140 is presented with a video of the patient's actual bodily movements, but one in which one or more portions of the patient's body have anonymized through computer generated renderings of those portions.

In some embodiments, cameras 64 are adapted to automatically identify a three-dimensional estimate of the patient's body from an analysis of the images captured thereby (including the depth sensors). In such embodiments, the generic rendering of the patient's body may be performed by adding a generic overlay on top of the detected patient skeleton. In some embodiments, this addition of a generic overlay onto the skeleton may be carried out in one or more conventional manners, such as using the OpenPTrack software developed by the University of California, Los Angeles (UCLA) and its Center for Research in Engineering, Media, and Performance (REMAP). The OpenPTrack software creates a scalable, multi-camera solution for group person tracking and version 2 (V2, Gnocchi) includes object tracking and pose recognition functionality. Various libraries may be utilized in the performance of one or more of these functions, such as the OpenPose library that is available from the UCLA REMAP project. Other software may also, or additionally, be utilized for detecting the position of the patient's body and generating an anonymized rendering of the patient's body.

Vision system 130 is configured to display a sequence of (i.e. a video of) the processed images 160 (FIG. 7) on one or more displays that are coupled to one or more devices that are in communication with vision system 130. Thus, a video of the processed images 160 may be shown on display 52 of patient support apparatus 20, on display 96 of electronic device 72, and/or on other displays. In some embodiments, the video of processed images 160 is a continuous stream that is forwarded to one or more electronic devices 72 that are associated with authorized caregivers. Alternatively, the video of processed images 160 is forwarded to one or more devices (e.g. electronic devices 72) only in response to one or more defined events and/or one or more requests from a caregiver or other authorized individual. With respect to defined events, controller 78 may be configured to begin transmitting a video of the patient (that may be modified by controller 78 to include processed images 160, or that may be forwarded to server 114 for server 114 to modify to include processed images) in response to an alert condition being detected by one or more of the sensors onboard patient support apparatus 20. For example, when exit detection system 82 detects a patient exit, controller 78 may be configured to automatically begin transmitting video from one or more of its cameras 64 to server 114, and server 114 may then modify this video to include processed images 160 and then forward it to one or more electronic devices 72.

Alternatively, controller 78 may be configured to transmit video from one or more cameras at all times, or substantially all times, to server 114. In such embodiments, server 114 may be configured to automatically forward all, or segments, of the processed images 160 to one or more electronic devices 72 at specific times (e.g. in response to a request and/or the occurrence of a predefined event).

In at least one embodiment, controller 78 and server 114 are configured to deliver to an electronic device 72 a processed video (e.g. comprised of processed images 160) of the patient automatically in response to exit detection system 82 issuing an exit alert (i.e. the patient exited or is in the process of exiting). Still further, in such embodiments, server 114 is configured to forward the exit alert (which is forwarded by controller 78 to server 114 in one or more data messages 154) to the same electronic device 72, which, in at least some embodiments, is programmed to make an audible sound, vibrate, and/or illuminate one or more lights in response to the receipt of the exit alert. In this manner, the caregiver associated with electronic device 72 will not only be alerted to the bed exit alert, but he or she will be able to view the patient's movement in substantially real time on display 96. The caregiver is therefore not only presented with notification of the exit alert, but also a visual depiction of the patient's movement. This can help the caregiver assess the urgency of his or her response to the exit alert. For example, if the exit alert has been accidentally triggered, or the patient has decided to return to patient support apparatus 20 after initially attempting to exit, the patient's movement will be displayed on display 96 and the caregiver should be able to see if the exit alert was accidentally triggered and/or if the patient has returned to patient support apparatus 20.

In addition to, or in lieu of, rendering all or a portion of the patient's body, vision system 130 may be configured to render all or a portion of patient support apparatus 20. That is, vision system 130 may include patient support apparatus rendering 164 within processed images 160 (FIG. 7). As with patient rendering 162, patient support apparatus rendering 164 is generated such that it matches the actual position of the portions of the patient support apparatus 20 that appear in the images captured by camera(s) 64, and moves as those portions may move. Patient support apparatus rendering 164, like patient rendering 162, may also be a whole rendering or a partial rendering. Similarly, patient support apparatus rendering 164 may generated with shades of a single color (that may or may not be the same color used for patient rendering 162). Still further, patient support apparatus rendering 164 may be generated by controller 78, server 114, or a combination of the two.

It will, of course, understood that any or all of the image modification that is reflected in processed images 160 and discussed herein as being carried out by controller 78 and/or server 114 could alternatively be carried out, either partially or wholly, by the one or more processors that are integrated into one or more of the cameras 64.

Figure 8:
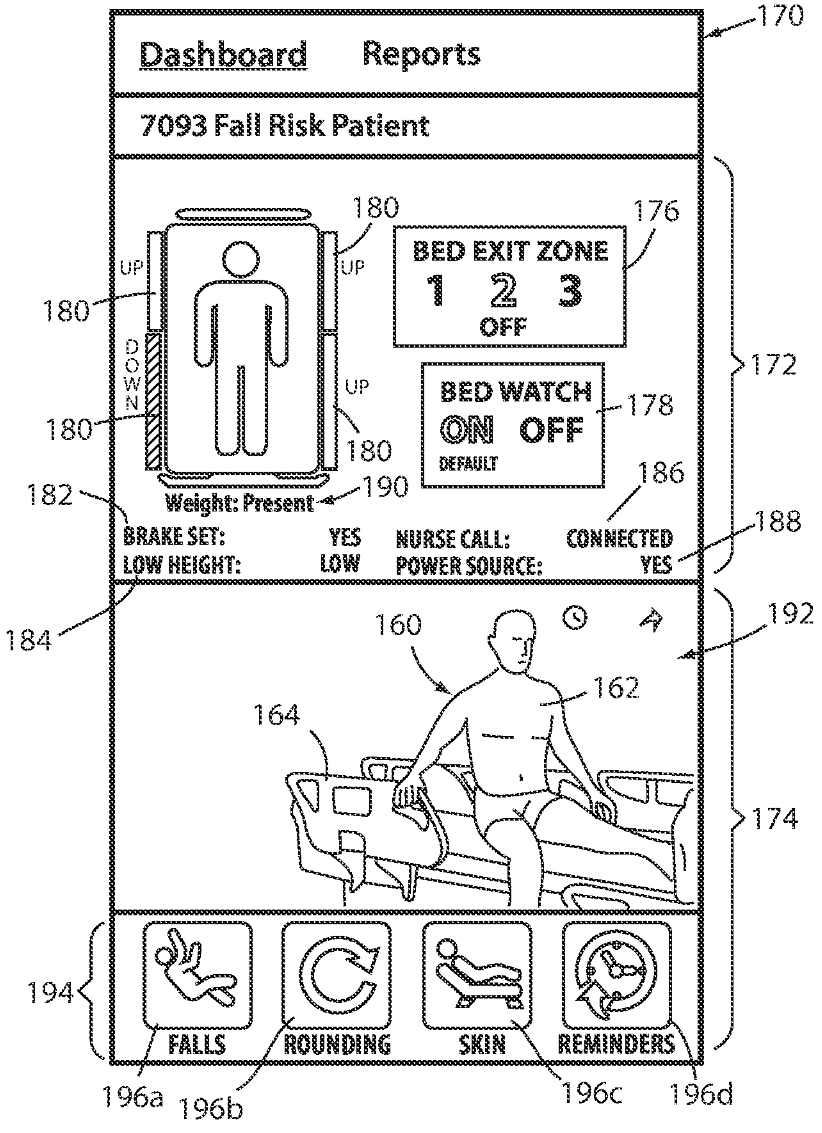
FIG. 8 is an example of a screen that may be displayed on one or more of the electronic devices described herein.

FIG. 8 illustrates one example of a screen 170 that may be displayed on electronic device 72 that is in communication with patient support apparatus server 114. Screen 170, in some embodiments, is generated by the software app 100 stored in memory 92 of electronic device 72. Software app 100 is configured to communicate with patient support apparatus server 114 via transceiver 94 and to receive the data and images shown on screen 170 from patient support apparatus server 114. Screen 170 includes an upper portion 172 and a lower portion 174.

Upper portion 172 displays various data regarding patient support apparatus 20 that is forwarded from patient support apparatus 20 in one or more data messages 154 to server 114, and server 114 then forwards that data to electronic device 72. This data includes an exit detection system indicator 176 that indicates what sensitivity, or zone, exit detection system 82 is currently armed with; a monitoring system indicator 178 that indicates whether an onboard monitoring system of patient support apparatus 20 is armed or disarmed; a plurality of siderail indicators 180 that indicate the up/down status of siderails 36; a brake status indicator 182; a low height (of litter frame 28) indicator 184; a nurse call system indicator 186 (that indicates whether patient support apparatus 20 is communicatively coupled to outlet 108 or not); a power source indicator 188 that indicates whether patient support apparatus 20 is currently receiving electrical power from electrical outlet 144 or not; and a weight indicator 190 that indicates whether a patient is currently present on patient support apparatus 20 or not (as determined by the weight detected by load cells 110).

Lower portion 174 (FIG. 8) includes an area 192 for displaying processed images 160, as well as a menu 194. Software application 100 is configured to display in area 192 a sequence of the processed images 160 that are received from patient support apparatus server 114. Thus, as was mentioned above, software application 100 may be configured in some embodiments to automatically display in area 192 a sequence of processed images 160 when the exit detection system 82 detects that the patient is attempting to, or has attempted to, exit from patient support apparatus 20. If electronic device 72 is a smart phone, then he or she is able to quickly see what the patient is doing on his or her smart phone when he or she has software application 100 running and the patient support apparatus 20 detects an exit alert condition. As was noted, this enables a caregiver, who may be positioned anywhere within the healthcare facility that allows his or her smart phone to access network 102, to remotely assess what the patient is doing and the urgency with which he or she wishes to respond.

Menu 194 may be provided on screen 170 in those embodiments of software application that are adapted to perform additional functions beyond the display of data associated with camera(s) 64. In such embodiments, the user is free to access the other functions of software application 100 by selecting one of menu icons 196*a, b, c* or *d*. In some embodiments, software application 100 is configured to include any or all of the same functionality as the caregiver assistance software application 124 disclosed in commonly assigned PCT patent application WO 2020/264140 filed Jun. 25, 2020 by Stryker Corporation and entitled CAREGIVER ASSISTANCE SYSTEM, the complete disclosure of which is incorporated herein by reference. In other embodiments, software application 100 may be configured to perform still other functions in addition to the image displaying functions and remote control functions described herein.

Figure 9:
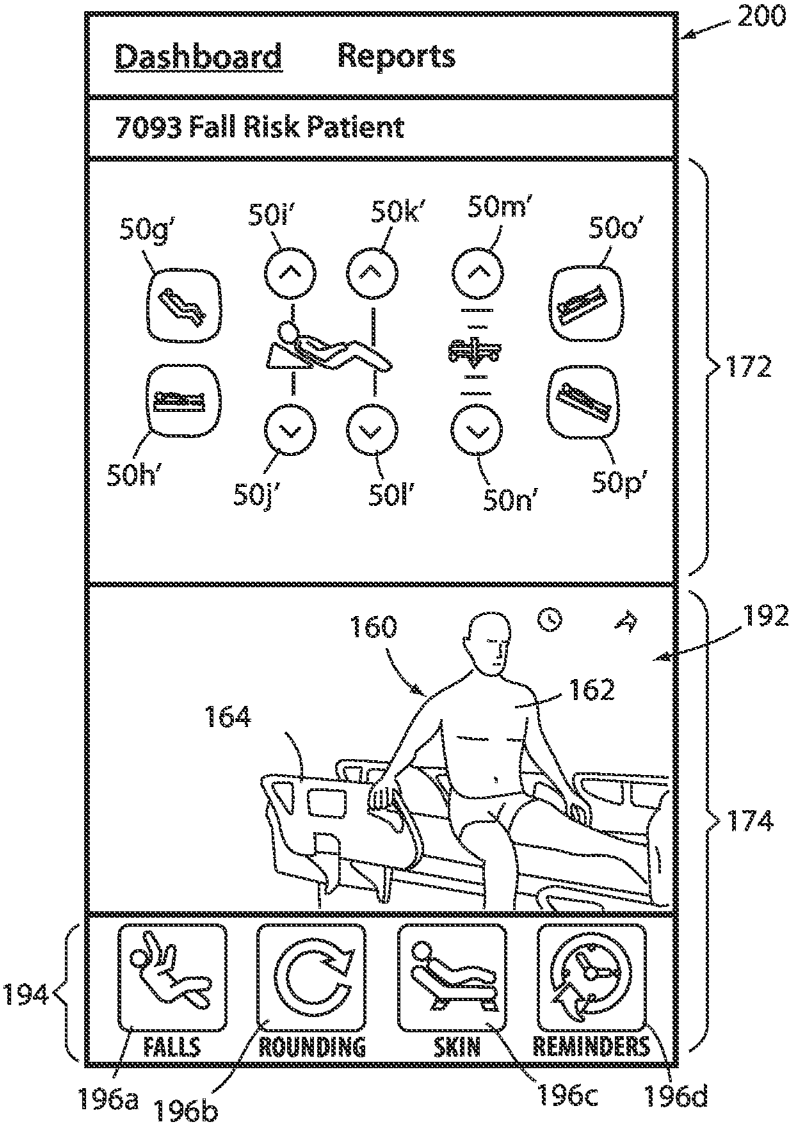
FIG. 9 is another example of another screen that may be displayed on one or more of the electronic devices disclosed herein.

FIG. 9 illustrates another example of a remote control screen 200 that may be displayed on display 96 of one or more electronic devices 72. Screen 200 includes the same lower portion 174 found in screen 170 (FIG. 8), and therefore does not need to be further discussed. Upper portion 172 of screen 200 is different from upper portion 172 of screen 170 (FIG. 8) in that the patient support apparatus data of screen 170 has been replaced with a set of motion controls 50*i*' through 50*p*'. Motion controls 50*i*'-50*p*' are adapted to control the same aspects of patient support apparatus 20 as motion controls 50*i*-50*p* of motion control screen 62 (FIG. 2). Motion controls 50*i*'-50'*p*, however, are displayed on the display 96 of electronic device 72 while motion controls 50*i*-50*p* are displayed on display 52 of patient support apparatus 20.

Server 114, electronic device 72, and/or patient support apparatus 20 are configured, in at least one embodiment, to drive one or more of the actuators 84, 86 of patient support apparatus 20 in response to the activation of one or more controls 50*i*'-50*p*' when one or additional conditions are satisfied, and to not drive the actuator(s) 84, 86 when those one or more additional conditions are not satisfied. In one embodiment, software application 100 is configured to disable motion controls 50*i*'-50*p*' whenever it is not also simultaneously displaying images of patient support apparatus 20 in display area 192. This disabling of controls 50*i*'-50*p*' is implemented in order to prevent a remotely positioned person from remotely moving one or more components of patient support apparatus 20 without that person also being able to simultaneously see the current position of those one or more components, as well as the surrounding environment (e.g. the range of motion of the component(s)). This helps ensure that any remote movement of patient support apparatus 20 is carried out safely without damaging patient support apparatus 20 or any objects positioned in the range of motion of patient support apparatus 20, as well as without injuring the patient, any other individuals that may be present on or near patient support apparatus 20.

In some embodiments, software application 100 is configured to simply not transmit any movement commands to server 114 when concurrent visual images of patient support apparatus 20 (from one or more cameras 64) are not simultaneously being displayed on display 96. In other words, controller 90 may be configured to disable controls 50*i*'-50*p*' whenever device 72 is not simultaneously displaying concurrent images of patient support apparatus 20. In another embodiment, instead of software application 100 disabling controls 50*i*'-50*p*', controller 90 may be configured to send movement commands to server 114 whenever a person presses on one or more of controls 50*i*'-50*p*', and server 114 may be configured to not forward those movement commands to patient support apparatus 20 if server 114 is not also simultaneously transmitting a video from camera 64 of patient support apparatus (whether modified or not) 20 to electronic device 72. In other words, in some embodiments, server 114 disables the functionality of remote controls 50*i*'-50*p*' by not forwarding corresponding movement commands to patient support apparatus 20. In still other embodiments, patient support apparatus 20 may be configured to disable remote controls 50*i*'-50*p*' by ignoring any movement commands it receives from server 114 unless it is simultaneously transmitting video from camera(s) 64 to server 114 that captures the range of motion of the movable components. In some such embodiments, controller 78 may be configured to require an acknowledgement from server 114 and/or electronic device 72 that it is receiving, and/or displaying, the video from camera 64 at the same time the movement commands triggered by controls 50*i*'-50*p*' are being transmitted to patient support apparatus 20 by server 114.

In the aforementioned embodiments, the remote controls 50*i*'-50*p*' are disabled by one or more of electronic device 72, server 114, and/or patient support apparatus 20 when video is not being concurrently displayed at the remote control device (i.e. electronic device 72). Further, the remote controls 50*i*'-50*p*' are enabled when video is being concurrently displayed at the remote control device. In these embodiments, it is up to the viewer of the remotely displayed video to analyze the video to ensure that the movement commands from controls 50*i*'-50*p*' are sent to patient support apparatus 20 when the corresponding movement is safe to carry out without risking injury to the patient, to patient support apparatus 20, and/or to other objects or people within the room.

In an at least one alternative embodiment, vision system 130 is configured such that the video from camera(s) 64 is automatically processed to determine if an obstacle is present in the movement path of the component that is to be moved by one of controls 50*i*'-50*p*', and to automatically disable or enable controls 50*i*'-50*p*' based on this automatic analysis. In such embodiments, the determination of whether it is safe to move a component of patient support apparatus 20 is carried out automatically by vision system 130. In such embodiments, it is not necessary to transmit video to electronic device 72 in order to enable one or more of controls 50*i*'-50*p*'. Instead, it is merely necessary for server 114 and/or controller 78 to determine that no obstacle is present within the movement path of the component that is being controlled remotely by one of controls **50*i*'-50*p*', as well as, in some cases, that one or more additional criteria are met for safely moving the desired components. Such additional criteria may include the absence of a patient on patient support apparatus 20** or still other criteria.

In those embodiments where controller 78 and/or server 114 are configured to automatically analyze the video from one or more of cameras 64 to determine if any obstacles are present in the movement path of a movable component of patient support apparatus 20, controller 78 and/or server 114 utilize the attribute data stored in database 124 that defines the movement capabilities of patient support apparatus 20. This attribute data, as discussed previously, indicates which components are movable, the extent of their movement, the location of those components, and the location or their movement paths.

It will be understood that whenever any of controls **50*i*'-50*p*' are disabled, whether by electronic device 72, server 114, or patient support apparatus 20, such disablement does not apply to the local controls 50*i*-50*p* that are part of, or displayed on, patient support apparatus 20 itself. In other words, it is only the remote controls 50*i*'-50*p*' that are disabled, not the local controls. This allows a user positioned on or adjacent to patient support apparatus 20 to move one or more components of patent support apparatus 20 regardless of the image data being captured by camera(s) 64**.

It will also be understood that in any of the embodiments discussed herein where software app 100 includes a remote control function (and therefore displays a screen like remote control screen 200 of FIG. 9), any one or more of patient support apparatus 20, server 114, and/or electronic device 72 may be configured to generate and/or receive a success or failure message when the remote controlled movement of a component of patient support apparatus 20 is disabled or completed, respectively. In other words, if the user presses on one of controls **50*i*'-50*p*', but system 130 has disabled that control, patient support apparatus 20, server 114, and/or electronic device 72 may generate a failure message that is displayed by controller 90 on display 96 to inform the user that the remote control of the movement of one or more components of patient support apparatus 20 was not successful. Similarly, if the user presses on one of controls 50*i*'-50*p*', and system 130 has enabled that control, patient support apparatus 20, server 114, and/or electronic device 72 may generate a success message that is displayed by controller 90 on display 96 to inform the user that the remote control of the movement of one or more components of patient support apparatus 20** was successful.

In some embodiments, vision system 130 is configured to lock out one or more controls 50 on patient support apparatus 20 such that the patient is not able to utilize those local controls. This local locking out of one or more controls 50 on patient support apparatus 20 is separate from and independent of the disabling of the remote controls **50*i*'-50*p*' discussed above. In such embodiments, vision system 130 analyzes the video from camera(s) 64 to identify the position of the patient, and locks out the desired controls whenever the patient is identified as trying to activate those controls. Thus, for example, if one of control panels 54*a* and/or 54*b* include a control for disarming exit detection system 82 and/or the onboard monitoring system, vision system 130 automatically disables those disarming controls whenever it detects that the patient is reaching for these controls. In some embodiments, vision system 130 may be configured to automatically disable an entire control panel (e.g. control panel 54*b*) from operating whenever the patient reaches to activate a control 50 positioned thereon. In either of these embodiments, vision system 130 does not disable any of the controls 50 on patient support apparatus 20 when a caregiver attempts to utilize them. Instead, one or more of the controls 50** are only disabled from patient use (and/or non-caregiver use).

In carrying out the disablement function of one or more local controls 50 for patient usage, controller 78 and/or server 114 utilizes attribute data from database 124 to analyze the images captured by camera 64. This attribute data includes data identifying the location and functionality of the control panels 54 on the patient support apparatus. It may also include attribute data regarding the caregivers that allows vision system 130 to identify caregivers from the images captured by camera 64.

In some embodiments, patient support apparatus 20 includes a settings screen that is displayable on display 52 and that allows an authorized user to select which local controls are to be disabled for usage by the patient, and which local controls are to be enabled for usage by the patient. In such embodiments, the selection of the enabled and disabled patient controls is utilized by vision system 130 to determine what controls are to be disabled when it detects that a patient is reaching toward one of those controls. Alternatively, or additionally, server 114 may be configured to display a screen that includes the same settings screen for allowing an authorized user to select which controls are to be disabled and enabled for patient usage. In either case, patient support apparatus 20 and server 114 communicate with each other to ensure that, when controller 78 and/or server 114 detects that the patient is reaching for a particular control—by analyzing the images from camera(s) 64—controller 78 and/or server 114 know whether or not to disable one or more controls adjacent to the patient's reaching hand.

Figure 10:
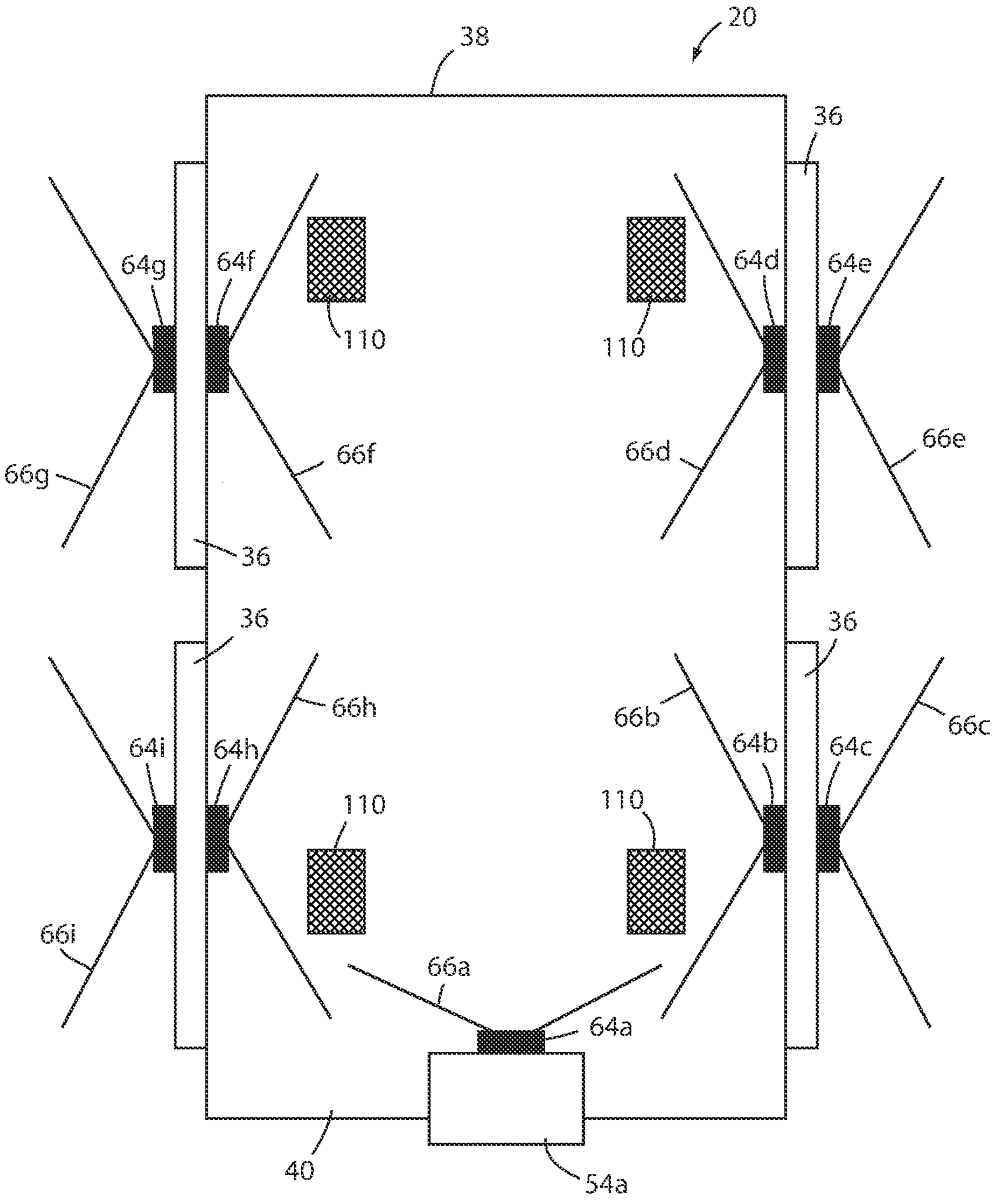
FIG. 10 is a block diagram of another embodiment of the patient support apparatus that includes a plurality of cameras.

FIG. 10 illustrates an alternative embodiment of patient support apparatus 20 that includes multiple cameras 64. Specifically, patient support apparatus 20 of FIG. 10 includes nine cameras **64*a-i*. Each camera includes a respective field of view 66*a-i*. In addition to a camera 64*a* positioned on the back side of control panel 54*a* (in the same manner as shown in FIG. 5), patient support apparatus 20 of FIG. 10 includes a pair of cameras mounted to each of the four siderails 36. A first one of the pair of cameras 64 is mounted to an interior side of the siderail 36 and a second one of the pair of cameras 64 is mounted to an outer side of the siderail. The inner mounted cameras (64*b*, 64*d*, 64*f*, and 64*h*) include respective fields of view that capture all or a portion of the patient when the patient is supported on patient support apparatus 20. The outer mounted cameras (64*c*, 64*e*, 64*g*, and 64*i*) include respective fields of view that capture the surrounding environment of patient support apparatus 20. All of the outputs from the cameras 64*a-i* are fed to controller 78 for processing in any of the manners discussed herein, including forwarding all or a portion of the outputs to server 114 for further processing and/or transmission to one or more electronic devices 72**.

In some embodiments, either or both of controllers 78 and server 114 of vision system 130 are adapted to stitch together the images from two or more of the cameras **64*a-i* to form a combined image. In some embodiments, the combined image is generated in a manner that present the viewer with a different field of view than any of the individual cameras 64, even when those fields of view are added together. For example, in the embodiment shown in FIG. 10, the images gathered by two or more of the cameras having fields of view 66 facing toward the patient (when positioned on patient support apparatus 20) may be combined together to yield a combined image that has a plan view field of view (i.e. a field of view from above the patient). Thus, although no cameras 64 are positioned above the patient, a field of view from above the patient may be generated by controller 78 and/or server 114 by combining the image and depth data from multiple ones of the cameras 64. The combined images may be processed in any of the manners discussed herein (e.g. in any of the manners discussed with respect to processed images 160**).

It will be understood that substantial modifications can be made to the number of cameras 64, the location of the cameras 64, and/or the orientation of the cameras shown in FIG. 10. For example, in at least one alternative embodiment, a camera 64 is positioned on, or adjacent to, each of the four corners of patient support apparatus 20. In such embodiments, the cameras 64 may be integrated into the siderails 36, the footboard 34, and/or the headboard 32. Alternatively, the cameras 64 may be mounted to litter frame 28 and/or deck 30. These corner cameras 64 may be provided in addition to those shown in FIG. 10, and/or they replace one or more of the cameras 64 shown in FIG. 10. The images captured by these corner cameras 64 may be stitched together each other and/or any one or more of the other cameras 64 shown in FIG. 10. The corner cameras may be configured to have fields of view that capture not only the support surface (i.e. deck 30) of patient support apparatus 20, but also the areas around the perimeter of the patient support apparatus 20. In some embodiments, the corner cameras 64 and/or the one or more of the cameras 64 shown in FIG. 10 are distributed about patient support apparatus 20 so that the entire perimeter of patient support apparatus 20 is captured by at least one camera so that a person cannot come into contact with any portion of patient support apparatus 20 without that person's image being captured by one or more of the cameras 64.

In any of the embodiments discussed herein, the stitching of multiple images together from different cameras 64 (whether positioned at a corner of patient support apparatus 20, or elsewhere) may utilize one or more conventional image merging and/or melding techniques such that inconsistent colors, textures, and/or other properties of the disparate images are gradually changed from along the border between the two images. In other words, the image melding techniques may be used to synthesize a transition region between the two images that melds together the images in a gradual manner having fewer visual artifacts. As another alternative, multiple images may be "gelled" together in a manner wherein the two images are not merged together along a pair of straight edges of each image, but instead are merged together with edges that fade into each other. In other words, instead of a straight dividing line between the two merged images, a faded or amorphous division is created between the two images in the combined image. Other types of merging and/or stitching techniques may also and/or alternatively be used.

Additional processing that may be performed by vision system 130, in at least some embodiments, includes analyzing the images from one or more cameras 64 to determine if the patient's breathing rate is above a defined threshold or below a defined threshold, analyzing the images from one or more cameras 64 to detect the presence of a ligature that presents a choking hazard for the patient, and/or analyzing the images from one or more of the cameras to identify within the images the patient's gown and/or the sheets on patient support apparatus 20.

Turning to the function of monitoring the patient's breathing, controller 78 and/or server 114 are configured in some embodiments to identify one or more boundaries of the patient's torso from the images captured by one or more of cameras 64, and to monitor the expansion and contraction of those one or more boundaries as the patient breathes (e.g. the rising and falling of the patient's chest). Alternatively, or additionally, the images from one or more cameras 64 may be analyzed by vision system 130 to monitor the expansion and contraction of the patient's nostrils. Still other techniques may be used to analyze the images to determine the patient's breathing rate.

After determining the patient's breathing rate from the images from camera(s) 64, controller 78 and/or server 114 are configured, in at least one embodiment, to compare this breathing rate to an upper limit and a lower limit. If the breathing rate exceeds the upper limit or is less than the lower limit, server 114 is configure to send an alert to the electronic device 72 associated with the caregiver assigned to care for the particular patient in the patient support apparatus 20. The upper and lower limits, in at least some embodiments, are configurable by one or more administrators 168 (FIG. 6) of the healthcare facility, such as by using a computer 166 that is in communication with server 114. Additionally, or alternatively, software app 100 may be programmed to allow a user of electronic device 72 to select the upper and lower breathing rates that will trigger an alert. In this manner, the caregiver can customize the breathing rate alerts for individual patients. Still further, in some embodiments, patient support apparatus 20 may be configured to allow an authorized user to enter and/or change the upper and lower breathing rates via one or more of the controls panels 54 positioned thereon. In some embodiments, server 114, electronic device 72, and/or patient support apparatus 20 may be installed with an upper and/or lower breathing rate that triggers an alert, and those default rates may be modified via one or more of control panels 54 on patient support apparatus 20, a computer (e.g. 166) accessing server 114, and/or by controls 98 of one or more electronic devices 72.

In some embodiments, vision system 130 may also or alternatively be configured to measure the amount of contraction/expansion of the patient's chest while they are breathing. Thus, in addition to the rate of breathing, vision system 130 may also determine a numeric indicator of the shallowness or depth of the patient's breath. This information may be utilized, in some embodiments, to determine if the patient is experiencing an asthma attack or not. Still further, in some embodiments, the upper and lower limits mentioned above for issuing a breathing rate alert may be based on the patient's initial baseline breathing rate. That is, instead of having a fixed upper limit and/or a fixed lower limit, the upper and lower limits may be percentages, or absolute values, above and/or below the patient's initial baseline breathing rate. The baseline breathing rate is determined when the patient initially enters patient support apparatus 20, and/or at other times.

In some embodiments, vision system 130 not only monitors the patient's breathing rate with respect to an upper and/or lower limit, but also monitors the rate of change of the patient's breathing rate. In such embodiments, an alert may be issued if the patient's breathing rate abruptly changes at a rate higher than a predetermined rate. Alternatively, or additionally, the rate of change of the patient's breathing rate may be monitored in combination with the patient's absolute breathing rate, and the breathing rate and rate of change of the breathing rate may be used individually or in combination to determine whether to issue an alert.

In those embodiments of vision system 130 that are adapted to monitor the patient's breathing rate, vision system 130 may be configured to examine visual images from camera(s) 64 to look for movement in the chest area and/or the belly area of the patient. In such embodiments, vision system 130 may also monitor changes in the patient from chest breathing to belly breathing, or vice versa. In some instances, the switching from one form of breathing (chest or belly) to another, coupled with changes in the breathing rate (e.g. above/below a limit and/or above a rate of change) causes vision system 130 to send an alert to one or more electronic devices 72 indicating that the patient may be experiencing a change that warrants the attention of a caregiver.

Additionally, or alternatively, in those embodiments of vision system 130 that are configured to monitor the patient's breathing, controller 78 and/or server 114 of vision system 130 may be configured to monitor the patient's breathing by detecting one or more edges of the patient's chest and/or belly. Movement of those edges when one or more of the other edges of the patient's body (e.g. the patient's legs, neck, hips, arms, etc.) does not move are interpreted generally by controller 78 and/or server 114 as breathing movements, while movement of the edges of the patient's chest and/or belly that occurs simultaneously with movement of other portions of the patient's body is generally interpreted as a gross movement of the patient that is separate from their breathing movement.

When vision system 130 is configured to analyze the images from camera(s) 64 to search for the presence of a ligature within those images, controller 78 and/or server 114 may be configured to search for objects within those images that have the shape of a ligature. This includes analyzing the shape of the sheets on the patient support apparatus and detecting when one or more of the sheets are rolled up into a ropey condition that could be looped around the patient's neck. When vision system 130 detects the presence of a ligature, it issues a warning to one or more caregivers by sending an alert from server 114 to one or more of the electronic devices 72.

In those embodiments of vision system 130 that are configured to detect a gown worn by the patient and/or to detect the sheets on patient support apparatus 20 (such as for ligature detection), vision system 130 utilizes one or more of the attributes of the gowns and/or sheets of that particular healthcare facility that are stored in database 124. That is, controller 78 and/or server 114 utilize the attributes of the gowns and/or sheets stored in database 124 when analyzing the images captures by camera(s) 64 in order to identify the gown and/or sheets that appear in the images. Identification of the gown is used by vision system 130 in some embodiments to identify the boundaries of the patient's body. Similarly, identification of the sheets is used by vision system 130 to distinguish between the patient's gown and the sheets, thereby further facilitating the identity of the patient's body. Identification of the patient's gown can be used in those embodiments of vision system 130 that monitor the patient's breathing to facilitate the identification of the patient's torso and/or chest.

Vision system 130, in some embodiments, is configured to also monitor locations around the perimeter of patient support apparatus 20 and/or underneath patient support apparatus 20 in order to automatically detect if a patient may be attempting to engage in acts of self-harm. Such acts of self-harm may include, in addition to using a ligature to hang oneself, attempts by the patient to crush one or more of their body parts by lowering components of patient support apparatus 20 (e.g. litter frame 28, siderails 36, deck sections 44, 46, 48, etc.) onto portions of their body. In order to detect these and other acts of self-harm, patient support apparatus 20 may include one or more cameras 64 positioned on a top side of base frame 22 that face upward toward siderails 36 and the underside of litter frame 28, and/or one or more downward facing cameras 64 positioned on the underside of litter frame 28, the underside of siderails 36, the underside of headboard 32 and/or the underside of footboard 34. Such cameras are positioned and oriented so that any body parts, or other objects, that are positioned in the movement range of litter frame 28 and/or siderails 36 (particularly the downward movement range of these components) will be within the field of view of one or more cameras 64. In this manner, the cameras 64 will be able to capture images of these body parts and/or objects so that vision system 130 can identify these body parts and/or objects and cause controller 78 instructing to stop or prevent downward movement of these components when a body part or other object is present in the downward motion path of these components.

In some embodiments, controller 78 and/or server 114 are configured to prevent downward movement of components of patient support apparatus 20 when any object—whether a patient body part or an inanimate object—is detected within the movement pathway of a component of patient support apparatus 20. If vision system 130 determines the object is not a human body part, it may simply disable downward movement of the corresponding component(s) of patient support apparatus 20 and take no further action. However, if vision system 130 determines that the object is a human body part, controller 78 and/or server 114 may be further configured to take one or more additional, such as automatically sending a message to an appropriate caregiver's electronic device 72 informing the caregiver of the detected body part in the movement path. This alerts the caregiver to take appropriate steps to respond to the situation. In some embodiments, controller 78 may also be configured to send a signal to the nurse call system server 126 when a patient's body part is detected in a movement path (and/or when a ligature is detected).

In embodiments, vision system 130 is adapted to automatically capture, and/or automatically mark, clips of videos that are relevant to certain activities performed using patient support apparatus 20, or performed on the patient, and/or that are performed within the vicinity of patient support apparatus 20. For example, in some embodiments, vision system 130 may automatically capture a video clip of patient support apparatus 20 encountering an obstruction during the movement of any of its components, a video clip of a patient attempting to use patient support apparatus 20 in a manner that causes self-harm, and/or a video clip of any events around the perimeter of, and/or within the main body of, patient support apparatus 20 that are of interest. In such embodiments, vision system 130 may automatically forward the video clip to one or more electronic device 72 so that remote caregivers can see the video on display 96. In some embodiments, as soon as an event of interest is detected by vision system 130, it may automatically begin streaming live video from one or more cameras 64 that are capturing the event to one or more electronic devices 72.

72

In some embodiments, vision system 130 is used to confirm and/or supplement sensors of other systems onboard patient support apparatus 20 and/or within the vicinity of patient support apparatus 20. For example, in some embodiments, vision system 130 is configured to confirm when any components of patient support apparatus 20 are moved in a manner the impacts an obstacle. That is, patient support apparatus 20 may include one or more force sensors that are positioned such that they detect forces resulting from a collision with an object when one or more components of the patient support apparatus 20 are moving. In such instances, controller 78 is configured to not issue an obstruction alert unless vision system 130 visually confirms that one or more components of patient support apparatus 20 actually ran into an obstruction. In other words, in some embodiments, vision system 130 is adapted to help avoid false obstruction detection alerts that might otherwise be issued by controller 78 if it relied solely on its force sensors for detecting a collision with an obstruction. In such embodiments, controller 78 only issues an alarm if vision system 130 visually recognizes contact with an obstruction at the same time that one or more force sensors onboard patient support apparatus 20 detect contact with an obstruction. False obstruction alarms can therefore be reduced.

In some embodiments, vision system 130 is adapted to work with, and confirm the outputs of, the perimeter load detection system described in commonly assigned U.S. patent application Ser. No. 63/335,863 filed on Apr. 28, 2022, by Lavanya Vytla et al. and entitled PATIENT SUPPORT APPARATUS FOR TREATING PATIENTS PRESENTING BEHAVIORAL HEALTH INDICIA, the complete disclosure of which is incorporated herein by reference. When combined with a system, such as that disclosed in the aforementioned '863 application, vision system 130 may automatically confirm whether a behavioral health event and/or a load applied to a perimeter of the patient support apparatus 20, is an actual event (as opposed to a false alarm) that warrants sending an alert to one or more caregivers, such as via one or more electronic devices 72. Vision system 130 may also, or alternatively, capture and/or mark clips of videos that encompass moments before, during, and after a perimeter load detection system of patient support apparatus 20 detects a load applied anywhere on the perimeters of patient support apparatus 20.

In some embodiments, vision system 130 is adapted to automatically analyze the images captured by cameras 64 to detect when a caregiver is positioned next to patient support apparatus 20 and/or within the same room as patient support apparatus 20. In some such embodiments, the caregivers may wear an ultra-wideband (UWB) badge that is adapted to communicate with a plurality of ultra-wideband transceivers that are positioned onboard patient support apparatus 20. The ultra-wideband transceivers onboard the patient support apparatus 20 are adapted to automatically determine the location of the caregiver's badge, read an ID from the badge, and use the ID to confirm that the badge is one that belongs to a caregiver. In some embodiments, vision system 130 is adapted to work in conjunction with such a UWB system to confirm that the ultra-wideband badges detected by the UWB transceivers onboard patient support apparatus 20 are indeed worn by a caregiver. Alternatively, or additionally, the UWB badges and transceivers may be used by vision system 130 to confirm whether facial recognition, and/or other caregiver detection techniques, have accurately determined that a caregiver is positioned next to a patient support apparatus 20. That is, if visual processing of the images from cameras 64 leads to vision system concluding that a caregiver is positioned adjacent patient support apparatus 20, vision system 130 may receive, request, or otherwise use data from the UWB system to confirm the presence of a caregiver adjacent to the patient support apparatus 20. In some embodiments, the UWB system used to detect caregiver-worn badges may include any of the structures, function, and/or features of the UWB badge system disclosed in commonly assigned U.S. patent application Ser. No. 63/356,061 filed Jun. 28, 2022, by inventors Krishna Bhimavarapu et al. and entitled BADGE AND PATIENT SUPPORT APPARATUS COMMUNICATION SYSTEM, the complete disclosure of which is incorporated herein by reference.

In some embodiments, vision system 130 is configured to visually monitor the position of one or more tagged items and to issue an alert if those tagged items are moved to another location. That is, in some embodiments, a healthcare facility may apply a visual tag to any item that it doesn't want removed from a particular area of the healthcare facility. The visual tags have visual attributes (e.g. size, shape, color, etc.) that are entered into database 124 and used by vision system 130 to visually recognize these tags when they are positioned within the field of view of any of the cameras 64 of vision system 130. When vision system 130 recognizes one of these visual tags within the images captured by one or more cameras 64, it determines the location of the tag and monitors that location to see if it changes. If it changes by more than a threshold, such as being moved out of the room in which it is currently being used and/or out of the field of view of one or more cameras 64, vision system 130 is configured to issue an alert to one or more caregivers indicating that an tagged object has been moved.

It will be understood that, although the foregoing discussion about detecting body parts of the patient has referenced the "patient's" body parts, vision system 130 does not need to be configured to recognize or distinguish the patient from other individuals. Instead, vision system 130 is configured to prevent downward movement of components of patient support apparatus 20 (and/or send messages to caregivers) when any human body parts are detected in the movement path of components, or when any ligatures are detected that might be used by any human. In other words, vision system 130 need not be configured to visually distinguish the patient assigned to patient support apparatus 20 from any other humans, but instead is configured to help prevent any individual from using patient support apparatus 20 to administer self-harm.

Vision system 130 may also be configured to automatically recognize mattress straps or brackets that are used on patient support apparatus 20 to secure mattress 42 thereto. Such straps or brackets may be a source of a ligature, and vision system 130 includes visual attributes of these straps and/or brackets so that it can more easily recognize them in the captured images, and process those images to see if the straps and/or brackets are being used to form a ligature or other tool of self-harm.

In some embodiments, vision system 130 uses one or more image subtraction techniques to determine the position of outline of the patients' body. That is, in some embodiments, the depth sensors that are included within camera(s) 64 are used to take one or more baseline snapshots of the patient support apparatus 20 when the patient is not present on the patient support apparatus 20. After the patient is present, depth sensor snapshots are taken and the difference between the depth sensor snapshots taken when the patient is present and when the patient is not present are used to identify the patient's body within the images (including the distance between the camera(s) 64 and each of the portions of the patient's body).

In some embodiments, the baseline image of the patient is automatically captured by one or more camera(s) 64 when the patient support apparatus 20 has its onboard scale system zeroed. This scale zeroing process is performed when the patient support apparatus 20 is empty of the patient, and therefore provides an opportunity for vision system 130 to capture baseline images of patient support apparatus 20 with no patient present. In such embodiments, controller 78 may be configured to automatically save a snapshot (or multiple snapshots) captured from one or more camera(s) 64 in response to the user activating the scale zeroing control (not shown) that is present on one or more of the control panels 54.

In some embodiments, controller 78 is configured to capture a baseline image of the patient on the patient support apparatus 20 when he or she is initially positioned thereon. This baseline image is then used by system 130 as a reference for determining subsequent patient movement. That is, subsequent images are taken periodically of the patient, and those subsequent images are compared to the baseline image of the patient when he or she was initially positioned on the patient support apparatus. The difference between the subsequent image and the baseline image provides an indication of how far the patient has moved. In some embodiments, this amount of movement is measured by vision system 130 and an alert, such as, but not limited to, an exit alert, is issued when the patient's movement exceeds a threshold amount (with respect to the baseline image).

In some embodiments, exit detection system 82 of patient support apparatus 20 is adapted to allow a user to enter a fall risk score (via one or more of control panels 54), wherein the fall risk score corresponds to an assessment of the patient's potential for falling. The fall risk score may be derived from a conventional fall risk analysis (e.g. a Morse fall risk score), or it may be derived from some other analysis. Once entered, controller 78 and/or exit detection system 82 may be configured to translate the fall risk score into a pre-selected sensitivity level for exit detection system 82 such that, when the caregiver arms exit detection system 82, it is automatically armed with a sensitivity level that has been selected by controller 78 and/or exit detection system 82 based on the patient's fall risk score.

In some embodiments, exit detection system 82 may be configured to work in conjunction with vision system 130 and/or vision system 130 may be utilized to detect patient exits either in conjunction with, or separately from, exit detection system 82. In some embodiments, vision system 130 may be adapted to monitor the movement of one or more parts of the patient's body and issue an alert when those monitored parts move (or move beyond a threshold). In such embodiments, vision system 130 may include a selection screen allowing the caregiver to monitor which parts of the patient it is to monitor for movement (e.g. left arm, right arm, left leg, right leg, head, etc.) and, after the caregiver selects the body parts to be monitored, vision system 130 thereafter analyzes the positon of the selected body parts in the images gathered from camera(s) 64 and issues an alert if one or more of the selected body parts moves past a threshold. The alert, as with all alerts from vision system 130, may be forwarded to one or more electronic devices 72 and/or it may be issued locally on patient support apparatus 20, and/or it may be forwarded to one or more other servers or other devices in communication with network 102.

Figure 11:
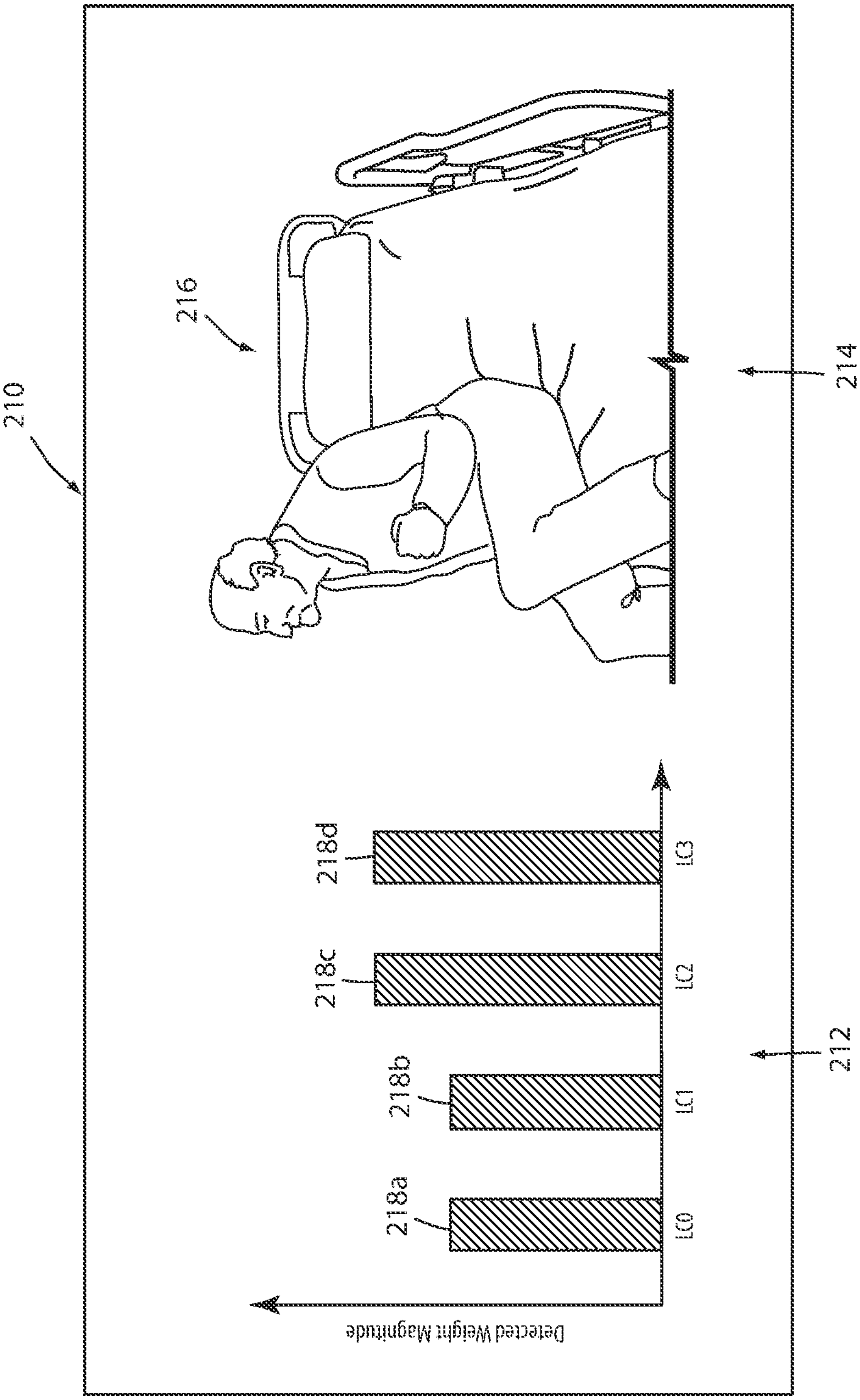
FIG. 11 is a screen shot of a synchronized video file illustrating a plurality of sensor readings synchronized with a video of a patient positioned onboard the patient support apparatus.

FIG. 11 illustrates a synchronization screen 210 that may be displayed in some embodiments of vision system 130 on one or more of displays 52, 96, and/or other displays (e.g. a display of computer 166 (FIG. 6)). Synchronization screen 210 displays a synchronized data file 112 (FIG. 4) that synchronizes the outputs from one or more sensors (such as sensors 88 and/or load cells 110) with the images captured by one or more cameras 64 (whether modified or unmodified). Thus, as can be seen in FIG. 11, screen 210 includes a left portion 212 that displays the outputs from one or more sensors and a right portion 214 that displays a video 216 captured by one or more cameras 64. In the particular example of FIG. 11, the left portion 212 shows the outputs 218*a-d* from four of the load cells 110 plotted in a bar graph format. Controller 78 of patient support apparatus 20 is configured to time stamp the readings from one or more of its onboard sensors (e.g. load cells 110 and/or one or more sensors 88), as well as to time stamp the images captured by one or more of its cameras 64. In some embodiments, patient support apparatus 20 is configured to have its clock automatically synchronized with the time maintained in another system and/or location (e.g. the time maintained by the network 102 of the healthcare facility, a source of local time, and/or a world clock). In such embodiments, patient support apparatus 20 may utilize any of the clock functions disclosed in commonly assigned U.S. Pat. No. 10,816,937 issued on Oct. 27, 2020, to Sidhu et al. and entitled PATIENT SUPPORT APPARATUSES WITH CLOCKS, the complete disclosure of which is incorporated herein by reference.

Controller 78 and/or server 114 is configured to use the time stamped sensor readings and camera images to generate one or more synchronized data files 112, and to then make those data files available for viewing on any of the displays that are part of, or in communication with, vision system 130. As was mentioned, the data file 112 shows the readings from one or more sensors over a period of time, along with the images captured from the camera(s) 64 over that same time period. That is, the sensor readings and images are displayed in a synchronized fashion so that, at any given moment, the image shown in right portion 214 corresponds to an image that was taken at the same time that the sensor readings shown in left portion 212 were taken. Because the data file 112 is a video file, it will be understood that the example screen 210 shown in FIG. 11 is merely one image from such a video file, and that both the position of the patient shown in the video 216 of right portion 214 will change, as will the readings 218 from the load cells 110 shown in left portion 212.

In some embodiments, controller 78 and/or server 114 are configured to stream the synchronized data file 112 to one or more electronic devices 72 in real time, or near real time (within one or several seconds) so that remotely positioned personnel can view the sensor readings and video images in real time, or nearly real time. The synchronized data file may also be stored in memory 80, a memory of server 114, and/or memory 92 of one or more electronic devices 72 for viewing at other times.

It will be understood that, although FIG. 11 illustrates a synchronized data file 112 that synchronizes the outputs from a plurality of load cells 110 with a video 216 of the patient's movement, vision system 130 may be configured to synchronize one or more videos 216 with one or more other sensor readings other than load cell readings. Thus, for example, vision system 130 may be configured to synchronize one or more videos 216 with one or more vital sign sensors, one or more sound, temperature, and/or light sensors, and/or still other types of sensors. Still further, the sensors that vision system 130 is configured to synchronize one or more videos 216 with do not need to be sensors that are incorporated into patient support apparatus 20, so long as those sensor reading are available to patient support apparatus 20 and/or server 114 and include a time stamp (or are received in near real time so that patient support apparatus 20 and/or server 114 can time stamp them). Thus, for example, controller 78 and/or server 114 may be configured to generate a synchronized data file from sensor readings taken from one or more separate devices, such as a DVT pump, a heart monitor, a patient monitor, a blood pressure sensor, a perfusion sensor, etc.

It will also be understood that the video 216 that is incorporated into the synchronized data file 112 may be a video that is unedited or it may be a modified video. When video 216 is a modified video, it may be modified in any of the manners discussed herein (e.g. it may be comprised of multiple videos stitched together, it may include one or more computer renderings, and/or it may be modified in still other manners).

In some embodiments, vision system 130 is configured to generate a synchronized data file 112 that also identifies the patient. The patient's identity, in some of these embodiments, may be displayed at any suitable location on synchronization screen 210. In some such embodiments, the patient's first or last initials may be utilized in lieu of the patient's full name, thereby preserving some anonymity of the patient. The patient's name may be determined via server 114 communicating with one or more of EMR server 120, ADT server 118, and/or another server on network 102.

In addition to, or in lieu of, identifying the patient's name, vision system 130 may generate synchronized data file 112 in a manner that identifies the device from which the sensors readings were taken and/or the sensors themselves. This identity may be displayed on screen 210 adjacent to the sensor readings from that particular device. In some embodiments, the identity may comprise a serial number, a model number, a device type, and/or other identifying information. Additionally, or alternatively, the device identification may include characteristics of the device, such as its room location. Thus, as an example, vision system 130 may specify the model of patient support apparatus 20, its location, and/or other identifying information next to the load cell readings shown in left portion 212 of synchronization screen 210 (FIG. 11).

Figure 12:
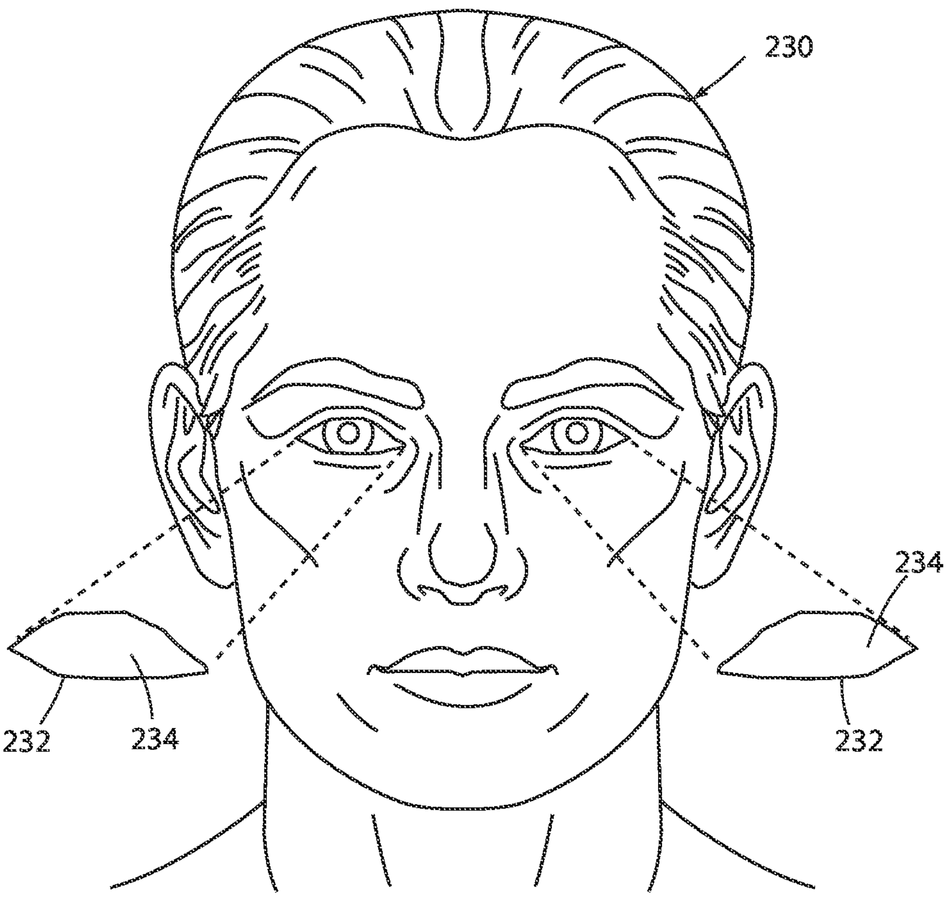
FIG. 12 is an example of a patient's face and the edges of the patient's eyes that may be monitored in one or more embodiments of the vision system disclosed herein.

FIG. 12 illustrates one example of a patient's facial image 230 that has been captured by one or more camera(s) 64 of vision system 130. In some embodiments of vision system 130, controller 78 and/or server 114 are configured to monitor movement of the patient's eyes and provide information regarding the patient's eye movement to one or more electronic devices 72 that are associated with caregivers assigned to that particular patient. In the example shown in FIG. 12, vision system 130 is configured to detect a set of edges 232 that partially, or wholly, define the boundaries of the patient's eyes. While edges 232 are pictured in FIG. 12 as being separate from the actual eyes of the patient in image 230, this is merely done for clarity purposes. Further, the size of edges 232 has been magnified in FIG. 11 to a size greater than the actual eyes of the patient in image 230. This too has been done for clarity purposes.

Vision system 130 (e.g. controller 78 and/or server 114) is configured to monitor changes in the shape of the edges 232 while the patient is positioned on patient support apparatus 20. The shape changes are monitored for the frequency at which the changes occur (which is indicative of the frequency of the patient's eye movement), the amount of change in the shape (e.g. how many millimeters, or fractions thereof, the edges 232 move), the direction in which the shape changes (up/down, left/right, diagonal, etc.), and/or other characteristics.

Vision system 130 may also be configured to monitor changes in the depth within an interior region 234 of the eye images. Such depth changes are detected by the one or more depth sensors that are incorporated into camera(s) 64, and such changes are also indicative of the patient's eye movement. This is because the front of the patient's eyeball is not perfectly spherical, and as a result, the distance (i.e. depth) between the depth sensor and different points within region 234 will change as the patient moves his or her eyes. Vision system 130 looks for these changes in depth to detect eye movement, in at least some embodiments.

In those embodiments of vision system 130 that monitor the patient's eye movement, controller 78 and/or server 114 may also monitor the colors within the images captured by camera(s) 64 to detect the patient's eye movement. That is, when the patient's eyes are open, vision system 130 may be configured to identify the patient's iris and/or pupil within region 234 by their color differences from the generally white areas of the patient's eyes. After identifying the iris and/or pupil within region 234, vision system 130 is configured to track the movement of one or both of these.

It will be understood that the monitoring of the patient's eye movement by tracking the movement of the patient's pupils, irises, and/or other features of the patient's eye is an activity that requires at least one of the patient's eyes to be open. However, the monitoring of the edges 232 for changes in shape and/or size, as well as the monitoring of depth changes within region 234, can both be carried out when the patient's eyes are open or closed. Thus, in at least some embodiments, vision system 130 is configured to monitor the patient's eye movements both when the patient's eyes are open as well as whey they are closed.

In some embodiments of vision system 130, the particular aspects of the patient's eyes that are monitored, as well as the particular eye events that lead to one or more notifications to a caregiver's electronic device 72, are configurable by a user of system 130. That is, in some embodiments, vision system 130 is configured to display on one or more of its associated displays (e.g. display 52, display 96, and/or a display of computer 166) a menu in which a user is able to select what eye conditions are to be monitored and/or what eye conditions warrant notification to one or more electronic devices 72. For example, in some embodiments, such as when a patient is in a coma, coming out of anesthesia, and/or in other situations, a caregiver is able to configure vision system 130 so that it notifies one or more devices 72 when the patient's eyes change from a state of generally little movement (e.g. a sleep state) to a more active state (e.g. an awake state). System 130 may also be configurable to provide notifications to electronic devices 72 when major changes are detected in the patient's eye movements. In general, vision system 130 may be configurable to provide notifications whenever any one or more of the following conditions is detected: REM sleep, patient agitation, slow and/or infrequent eye movement, changes in overall eye movement patterns, changes in frequency of eye movement, changes between sleep and awake states, whenever the patient's eyes open or close, etc.

In some embodiments of vision system 130 that are adapted to monitor the patient's eyes, one or more cameras

64 may be mounted high on a wall or on the ceiling of the room in which patient support apparatus 20 is positioned. Alternatively, or additionally, one or more cameras 64 may be mounted on one or more booms and/or arms that attach to patient support apparatus 20 and that position the camera (s) 64 at a location with an unobstructed view of the patient's eyes, and where the camera is closer to the patient's eyes than what might be possible for any of the cameras 64 that may be mounted directly to footboard 34 and/or siderails 36. The boom and/or arm may be movable so that it can be moved out of the way of the patient when he/she enters/exits patient support apparatus 20, as well as out of the way of a caregiver while that caregiver interacts with the patient.

Although cameras 64 are primarily described herein as being adapted to capture visible light images, it is to be understood that, in at least some embodiments of system 130, one or more of cameras 64 may be modified to include infrared image sensing devices, either in lieu of, or in addition to, their visual light image sensors. When equipped with one or more of such infrared image sensing devices, system 130 is able to capture images of the patient and/or patient support apparatus 20 even when the room is dark. The capturing of such infrared images utilizes existing ambient infrared light within the room, in some embodiments, and in other embodiments, utilizes one or more sources of infrared light that are provided as part of system 130. In addition to capturing images in dark or low-light conditions, utilizing one or more infrared cameras 64 also allows system 130 to detect thermal images. Server 114, controller 78, and/or electronic devices 72 may include software that is adapted to utilize such thermal images for carrying out any one or more of the functions described herein.

In some embodiments, vision system 130 is configured to retain the videos (whether processed or unprocessed) generated by camera(s) 64 and store them in memory for future access. In such embodiments, vision system 130 may be configured to allow different levels of access to these videos depending upon the user. For example, in some embodiments, certain viewers are only able to see the processed videos that have the generic renderings of all or a portion of the patient, thereby preserving the patient's anonymity. Certain other viewers, however, will be granted greater access and be able to see the images and/or videos that do not have the patient's identity obfuscated (i.e. anonymized). In some of these embodiments, the particular videos that are available for displaying to a user will be dependent upon the event(s) captured by the video. For example, in some embodiments, video of the patient in which the only the patient's face (or none of the patient) is obfuscated is made available to all authorized caregivers whenever the patient exits patient support apparatus 20. That is, all caregivers are able to see video of the patient's actual body when he/she exits from patient support apparatus 20. However, during non-exit time periods, those caregivers are only able to see video of the patient that has been processed to obfuscate the patient's face and/or body (e.g. video that includes generic renderings of the patient's head and/or other body parts). Other events besides bed exit, in some embodiments, may cause vision system 130 to display to authorized caregivers video that does not obfuscate the patient's identity, or that obfuscates the patient's identity to a lesser extent than what vision system 130 does when those other events are not transpiring. In any of the embodiments disclosed herein, the access of particular caregivers to particular types of videos captured by cameras 64 (e.g. those with different levels of obfuscation of the patient's identity) may be customized by authorized personnel of the healthcare facility utilizing patient support apparatus server 114.

It will be understood that vision system 130 may include any of the components, functions, software modules, and/or other features of the monitoring system disclosed in commonly assigned U.S. Pat. No. 10,121,070 issued Nov. 6, 2018, to Richard Derenne et al. and entitled VIDEO MONITORING SYSTEM, the complete disclosure of which is incorporated herein by reference. Further, vision system 130 may use any of the techniques, databases, tools, and/or other structures disclosed in the aforementioned U.S. Pat. No. 10,121,070 patent to carry out any one or more of the functions described herein.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A patient support apparatus comprising:
- a support surface adapted to support a patient thereon;
- a component;
- a powered actuator adapted to move the component;
- a control panel including a movement control adapted to control the powered actuator;
- a transceiver adapted to receive a movement command from a remote control positioned off-board the patient support apparatus;
- a controller in communication with the transceiver and a camera having a field of view that includes a range of motion of the component, the controller adapted to drive the actuator in response to receiving the movement command if the camera is simultaneously capturing a video stream that includes the component, to not drive the actuator in response to the movement command if the camera is not simultaneously capturing the video stream; and to drive the actuator in response to the activation of the movement control on the control panel regardless of whether the camera is simultaneously capturing the video stream.

2. The patient support apparatus of claim 1 wherein the camera is positioned onboard the patient support apparatus.

3. The patient support apparatus of claim 2 wherein the transceiver is adapted to transmit the video stream to the remote control.

4. The patient support apparatus of claim 2 further comprising a second camera positioned onboard the patient support apparatus, wherein the controller is further adapted to generate a stitched video stream comprised of a portion of the video stream from the camera and a portion of a second video stream from the second camera.

5. The patient support apparatus of claim 3 wherein the transceiver is further adapted to receive an acknowledgement from the remote control of the receipt of the video stream.

6. The patient support apparatus of claim 5 wherein the controller is further adapted to drive the actuator in response to receiving the movement command if the camera is simultaneously capturing the video stream and the controller has received the acknowledgement from the remote control, and to not drive the actuator in response to receiving the movement command if the camera is simultaneously capturing the video stream but the controller has not received the acknowledgement from the remote control.

7. The patient support apparatus of claim 1 further comprising a litter frame supported by a pair of lifts, and wherein the component is the litter frame.

8. The patient support apparatus of claim 1 wherein the support surface includes a Fowler section adapted to pivot about a generally horizontal axis, and wherein the component is the Fowler section.

9. The patient support apparatus of claim 1 wherein the transceiver is a WiFi transceiver adapted to communicate with a wireless access point of a local area network of a healthcare facility.

10. The patient support apparatus of claim 9 wherein the remote control is an electronic device adapted to communicate with the wireless access point of the local area network, and to send the movement command to a server on the local area network that is forwarded by the server to the patient support apparatus.

11. The patient support apparatus of claim 1 further comprising a second control panel, the second control panel including a second control adapted to carry out a particular function when activated, wherein the second control panel includes a face adapted to face away from the patient when the patient is positioned on the support surface.

12. The patient support apparatus of claim 11 wherein the controller is further adapted to analyze the video stream to determine if the patient is attempting to activate the second control panel and to disable the second control if the controller determines that the patient is attempting to activate the second control.

13. The patient support apparatus of claim 12 further comprising an exit detection system, wherein the second control is adapted to disarm the exit detection system when the second control is activated.

14. The patient support apparatus of claim 12 further comprising an onboard monitoring system adapted to monitor a plurality of conditions on the patient support apparatus and to issue an alert if at least of the conditions is in an undesired state, and to not issue the alert if none of the conditions are in the undesired state, and wherein the second control is adapted to disarm the onboard monitoring system when the second control is activated.

15. The patient support apparatus of claim 1 wherein the controller is further adapted to analyze the video stream to determine if a ligature is present within the field of view.

16. The patient support apparatus of claim 15 wherein the controller is further adapted to transmit a message to a server on a local area network of a healthcare facility if the controller detects the presence of the ligature.

17. The patient support apparatus of claim 1 wherein the controller is further adapted to identify the patient support apparatus in the video stream, to modify the video stream by replacing the patient support apparatus with a computer generated rendering of the patient support apparatus, and to transmit the modified video stream to an off-board device.

18. The patient support apparatus of claim 17 wherein the off-board device is a server on a local area network of a healthcare facility in which the patient support apparatus is positioned.

19. The patient support apparatus of claim 1 further comprising an exit detection system comprising a plurality of load cells, wherein the controller is further adapted to generate a synchronized data file, the synchronized data file including a visual representation of readings from the plurality of load cells synchronized with movement of the patient captured in the video stream, and wherein the controller is further adapted to transmit the synchronized data file to an off-board device.

20. The patient support apparatus of claim 19 wherein the off-board device is a server on a local area network of a healthcare facility in which the patient support apparatus is positioned.

* * * * *